(12) United States Patent
Okuda

(10) Patent No.: US 12,181,555 B2
(45) Date of Patent: Dec. 31, 2024

(54) 3-DIMENSIONAL REPRESENTATIONS OF POST-CONTRAST ENHANCED BRAIN LESIONS

(71) Applicant: THE BOARD OF REGENTS OF THE UNIVERSITY OF TEXAS SYSTEM, Austin, TX (US)

(72) Inventor: Darin Okuda, Coppell, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 18/425,964

(22) Filed: Jan. 29, 2024

(65) Prior Publication Data

US 2024/0168117 A1    May 23, 2024

Related U.S. Application Data

(63) Continuation of application No. 16/976,028, filed as application No. PCT/US2019/019652 on Feb. 26, 2019, now Pat. No. 11,885,861.

(Continued)

(51) Int. Cl.
*G01R 33/56* (2006.01)
*G01R 33/48* (2006.01)
(Continued)

(52) U.S. Cl.
CPC ..... *G01R 33/5608* (2013.01); *G01R 33/4822* (2013.01); *G01R 33/5601* (2013.01);
(Continued)

(58) Field of Classification Search
None
See application file for complete search history.

(56) References Cited

U.S. PATENT DOCUMENTS

| 6,381,486 B1 | 4/2002 | Mistretta et al. |
| 11,093,787 B2 | 8/2021 | Okuda et al. |

(Continued)

FOREIGN PATENT DOCUMENTS

| WO | WO 2017/147418 | 8/2017 |
| WO | WO 2018/005939 | 1/2018 |

OTHER PUBLICATIONS

International Search Report and Written Opinion issued in Corresponding PCT Application No. PCT/US2019/019652, dated May 8, 2019.

(Continued)

*Primary Examiner* — Dov Popovici
(74) *Attorney, Agent, or Firm* — Norton Rose Fulbright US LLP

(57) ABSTRACT

3D MRI images of the brain may be created and acquired. After administration of contrast, brain lesions and other abnormalities may be identified and isolated from the 3D MRI images, with each lesion serving as a region of interest (ROI). 3D region of contrast enhancement images may be created from segmented 3D MRI images and different regions of contrast enhancement of the brain lesion may be depicted. Saved regions of contrast enhancement may be converted into stereolithography format, maximum intensity projection (MIP) images, and/or orthographic projection images. Data corresponding to these resulting 3D region of contrast enhancement images may be used to create 3D printed models of the isolated region of contrast enhancement. Analysis of the 3D brain region of contrast enhancement images and the 3D printed region of contrast enhancement models may enable a more efficient and accurate way of determining brain lesion risk factors and effective treatment regimens.

2 Claims, 15 Drawing Sheets

Related U.S. Application Data

(60) Provisional application No. 62/635,288, filed on Feb. 26, 2018.

(51) Int. Cl.
    *G06N 20/00* (2019.01)
    *G06T 7/11* (2017.01)

(52) U.S. Cl.
    CPC ............... *G06N 20/00* (2019.01); *G06T 7/11* (2017.01); *G06T 2207/10088* (2013.01); *G06T 2207/30016* (2013.01); *G06T 2207/30096* (2013.01)

(56) References Cited

U.S. PATENT DOCUMENTS

| | | | | |
|---|---|---|---|---|
| 2011/0255761 | A1* | 10/2011 | O'Dell | G06T 7/0014 |
| | | | | 382/128 |
| 2015/0346303 | A1 | 12/2015 | Hu et al. | |
| 2017/0256056 | A1* | 9/2017 | Jain | G06T 7/143 |

OTHER PUBLICATIONS

Khawaja, Ashan; "Influence of Contrast Enhancement Methods in Brain Tumor Dection", *Biomedical and Bioinformatics Engineering*, pp. 29-34, 2016.2016.

Supplementary European Search Report issued in corresponding application No. 19757029.4 / PCTUS2019/019652 dated Nov. 4, 2021.

* cited by examiner

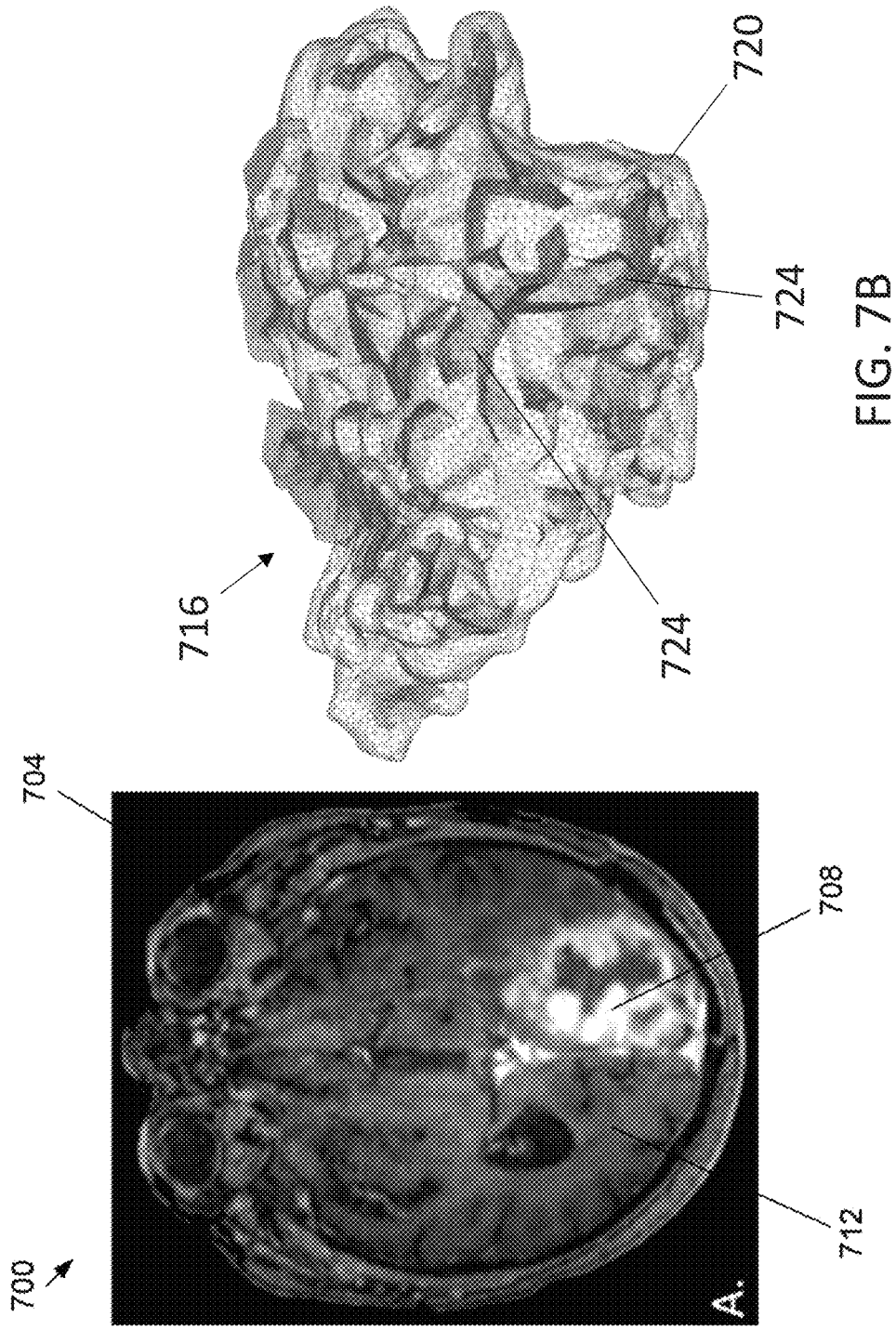

3-DIMENSIONAL REPRESENTATIONS OF POST-CONTRAST ENHANCED BRAIN LESIONS

CROSS-REFERENCE TO RELATED APPLICATIONS

This application is a continuation of U.S. patent application Ser. No. 16/976,028, filed Aug. 26, 2020, which is a national phase application under 35 U.S.C. § 371 of International Application PCT/US2019/019652, filed Feb. 26, 2019, which claims priority to U.S. Provisional Patent Application No. 62/635,288, filed Feb. 26, 2018, the contents of each of which are incorporated by reference in their entireties.

FIELD OF THE INVENTION

This disclosure relates generally to methods, apparatuses, and systems for creating 3-dimensional (3D) representations exhibiting spatial, surface, and structural characteristics of post-contrast enhanced brain lesions.

DESCRIPTION OF RELATED ART

The diagnosis of multiple sclerosis (MS) requires the fulfillment of both clinical and radiological criteria. This may include a determination of key radiological tenets such as a requisite number of lesions having a specific character (i.e. size, shape, and morphology) and spatial distribution patterns with involvement of periventricular, juxtacortical, infratentorial, and spinal cord regions. The effective application of the existing dissemination in space criteria may be hindered by the highly sensitive nature of MRI technology, the heterogeneity of lesions resulting from a variety of medical conditions, concomitant radiological features resulting from age-related changes and disease, and the lack of additional radiological characteristics beyond two-dimensional descriptions.

At present, the diagnosis of MS is usually made through the use of 2-dimensional (2D) MRI images. The implementation of certain imaging metrics, including the use of quantitative phase imaging, has improved lesion specificity. This may highlight the presence of central vasculature within lesions and distinct peripheral rings, suggesting the presence of iron within macrophages. The use of fluid-attenuated inversion recovery (FLAIR) MRI at 3 Tesla (T) and T2-weighted and susceptibility weighted imaging (SWI) at 7 T in larger patient groups has also been utilized to better characterize MS from non-MS lesions. A previously identified threshold of >40% was described for improving the specificity of MS lesions. However, this technique has been limited by the lack of appreciation of the central vessel in all orthogonal planes of view and the abundance of vessels intersecting lesions within the supratentorial region. Beyond these efforts, peripheral regions of hypointensity, presumed to be related to the presence of iron within macrophages, have also been described in MS patients.

Glioblastoma multiforme (GBM) is the most frequent high-grade glioma diagnosed annually, having a global incidence of 0.59-3.69 per 100,000 persons. Despite advances in molecular profiling, neuroradiology, and available treatments, the approximate 5-year survival rate of those with GBM is only 5%. Magnetic resonance imaging (MRI) data is invaluable in the surveillance of disease; however, determining the origin of new or advancing regions of contrast enhancement and the association of these findings with radiation necrosis, tumor recurrence, immune activity, or a combination of these factors represents a key area of clinical management given the prognostic and therapeutic implications.

Currently, there is no clear evidentiary standard regarding radiological definitions of disease advancement and the value of post-contrast features in identifying malignant transformation remains controversial. When observed, contrast enhancement signifies blood brain barrier permeability that may be the result of varied etiologies. Previous data suggests that tumor cell density and cellular mitosis appear to be highest in regions of contrast enhancement. The significance of distinct radiological patterns of enhancement were previously investigated; however, a remarkable prognostic signature has not yet been identified. In addition, the observed contrast enhanced data may be influenced by 06-methylguanine-DNA methyltransferase (MGMT) promoter methylation status. The routine evaluation of post-contrast imaging features is confined to 2-dimensional (2D), forced-perspective views. These 2D views limit the understanding of true spatial, surface, and structural patterns of 3D brain lesions. The lack of reliable contrast enhancement signatures may be the result of this limited approach.

Morphological, functional, and metabolic features have been studied in the past including 3,4-dihydroxy-6-[18F]-fluoro-L-phenylalanine (18-DOPA) PET, O-(2-18F-Fluoroethyl)-L-Tyrosine PET/MRI, apparent diffusion coefficient (ADC) maps, and susceptibility-weighted MRI and dynamic susceptibility contrast (DSC) perfusion-weight imaging (PWI) in efforts to identify radiological patterns associated with true tumor advancement. Studies focused on the value of contrast enhancement radiological phenotypes have also been explored. Texture analysis of post contrast imaging sequences has been used to differentiate between low and high grade gliomas pre-surgical intervention as well as between different types of brain tumors when incorporated into machine learning algorithms. The prognostic significance of 2D contrast patterns having "patchy and faint", "nodular-like", and "ring-like" characteristics in low grade gliomas was previously assessed with the nodular-like pattern and time-progressive contrast enhancement associated with poor prognosis following univariate analysis. Similar focal and nodular patterns of T1 contrast enhancement were also found to correlate with tumor recurrence in high grade gliomas, while thin, linear enhancement was associated with radiation necrosis. However, these investigations were limited to 2D MRI views which may account for the lack of an identified robust signal.

SUMMARY

This disclosure includes embodiments of methods, apparatuses, and systems for creating 3-dimensional (3D) representations exhibiting spatial, surface, and structural characteristics of post-contrast enhanced brain lesions. Some embodiments comprise a computer system having at least one processor that may be configured to receive one or more 3D images of a brain; enable an identification of one or more regions of contrast enhancement in the one or more 3D images of the brain; enable a segmentation of the one or more 3D images, the segmentation enabling an isolation of the one or more regions of contrast enhancement; enable a creation of one or more 3D region of contrast enhancement images based on the segmentation, the one or more 3D region of contrast enhancement images comprising one or more region of contrast enhancement characteristics; enable a comparison of the one or more region of contrast enhancement characteristics of the one or more 3D region of contrast enhancement images with one or more predetermined region of contrast enhancement characteristics; and enable a determination of a category of the one or more region of contrast enhancement based on a match between the one or more region of contrast enhancement characteristics of the one or more 3D region of contrast enhancement images and the one or more predetermined region of contrast enhancement characteristics. In some embodiments, the at least one processor may be able to communicate with a memory source and/or non-transitory computer readable medium to receive one or more instructions enabling the at least one processor to perform the actions disclosed above. In some embodiments, the at least one processor may be actively performing the actions disclosed above based on one or more instructions received from a memory source and/or non-transitory computer readable medium. In some embodiments, the at least one processor may be hardwired in such a way as to have the ability to perform and/or actually perform the actions disclosed above.

In some embodiments, the computer system may be further configured to enable the sending of 3D representation data corresponding to the one or more 3D region of contrast enhancement images, the 3D representation data configured to enable a creation of one or more physical 3D representations of the one or more regions of contrast enhancement. The one or more 3D images may comprise one or more maximum intensity projection (MIP) images, the MIP images configured to enable 3D spatial visualization of the regions of contrast enhancement. In some embodiments, the one or more 3D region of contrast enhancement images may comprise one or more orthographic projections in stereolithographic format. In some embodiments, the one or more physical 3D representations comprise may be fused filament 3D printed models. The one or more 3D images of the brain may comprise one or more isotropic magnetic resonance imaging (MRI) images. In some embodiments, the one or more region of contrast enhancement characteristics may comprise one or more of geometric characteristics, surface characteristics, and structural characteristics. In some embodiments, the one or more predetermined region of contrast enhancement characteristics may correspond to one or more lesion characteristics associated with one or more disease risk factors. In some embodiments, the at least one processor is further configured to use machine learning to generate at least one description for the one or more region of contrast enhancement characteristics and associate the at least one description with the category of the one or more region of contrast enhancement.

Some embodiments of the present methods include a method of creating 3-dimensional (3D) representations of post-contrast enhanced brain lesions that may comprise receiving, by a computer system comprising at least one processor, one or more 3D images of a brain; enabling, by the computer system, an identification of one or more regions of contrast enhancement in the one or more 3D images of the brain; enabling, by the computer system, a segmentation of the one or more 3D images, the segmentation enabling an isolation of the one or more regions of contrast enhancement; enabling, by the computer system, a creation of one or more 3D region of contrast enhancement images based on the segmentation, the one or more 3D region of contrast enhancement images comprising one or more region of contrast enhancement characteristics; enabling, by the computer system, a comparison of the one or more region of contrast enhancement characteristics of the one or more 3D region of contrast enhancement images with one or more predetermined region of contrast enhancement characteristics; and enabling, by the computer system, a determination of a category of the one or more regions of contrast enhancement based on a match between the one or more region of contrast enhancement characteristics of the one or more 3D region of contrast enhancement images and the one or more predetermined region of contrast enhancement characteristics.

Some embodiments of the present methods of characterizing and/or predicting behavior of a brain lesion include receiving a first set of one or more 3D images of a brain generated at a first time; receiving a second set of one or more 3D images of the brain generated at a second time that is later than the first time; for each of the first and second sets, and with at least one processor, identifying one or more regions of contrast enhancement in the set, segmenting the set to isolate the region(s) of contrast enhancement, and creating, based on the isolated region(s) of contrast enhancement, one or more 3D region of contrast enhancement representations comprising one or more region of contrast enhancement characteristics; and comparing one or more of the region of contrast enhancement characteristic(s) associated with the first set to one or more of the region of contrast enhancement characteristic(s) associated with the second set. Some methods comprise creating a 3D region of contrast enhancement representation that is indicative of one or more differences between one or more of the region of contrast enhancement characteristic(s) associated with the first set, and one or more of the region of contrast enhancement characteristic(s) associated with the second set.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

Any embodiment of any of the disclosed methods, systems, system components, or method steps can consist of or consist essentially of—rather than comprise/include/contain/have—any of the described elements, steps, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

BRIEF DESCRIPTION OF THE DRAWINGS

The following drawings illustrate by way of example and not limitation. For the sake of brevity and clarity, every feature of a given method or system is not always labeled in every figure related to that method or system. Identical reference numbers do not necessarily indicate an identical feature. Rather, the same reference number may be used to indicate a similar feature or a feature with similar functionality, as may non-identical reference numbers.

FIGS. 7A-D depict exemplary experimental analysis results from an implementation of the systems and methods described by an embodiment of the disclosure.

DETAILED DESCRIPTION OF ILLUSTRATIVE EMBODIMENTS

Utilization of 3-dimensional (3D) methods may provide a better understanding of what is observed on conventional 2D images along with new insights into the observed radiological features resulting from alterations in blood brain barrier physiology. This disclosure describes a practical and innovative approach to understanding 3D spatial, surface, and structural differences from brain MRI post-gadolinium data to improve the ability to differentiate between the effects of therapeutic interventions and disease progression in GBM patients. These 3D imaging and analytical techniques may easily be incorporated into studies for direct clinical application.

The disclosed methods can be applied to MRI contrast enhancement data that can then demonstrate remarkable 3D spatial, structural, and surface features between neurologically stable GBM patients and those with disease advancement. Using the disclosed systems and methods, spherical shapes and greater circumferential fullness can be identified in those patients with documented neurological decline suggesting the value of post-contrast 3D morphological data in identifying patients that require treatment regimen changes. There also appears to be a trend towards differences in the post-contrast enhanced tumor shell width and mean enhanced voxel intensities between clinical states. Additionally, the application of machine learning techniques using multi-parametric MRI features to identify tumor recurrence from pseudoprogression represents early stages of technical advancements that may result in more sensitive and specific solutions.

The embodiments discussed below describe systems, apparatus, and methods for creating 3-dimensional (3D) representations exhibiting shape and surface characteristics of post-contrast brain lesions/tumors. More specifically, the embodiments discussed below present 3D spatial visualization of the entire brain lesion and, more specifically, of particular regions of contrast enhancement of the brain lesion. These 3D images can provide geometric and surface characteristic data of the regions of contrast enhancement of brain tumors in comparison to certain disease states that may improve tumor risk and treatment determinations by leveraging imaging techniques that can be implemented into clinically acquired studies for direct clinical application. The embodiments discussed below also describe integrating the use of 3D printing software and hardware, allowing for tactile review of the observed findings on MRI to further elucidate the geometric and surface characteristics between varying region of contrast enhancement categories.

Figure 1:
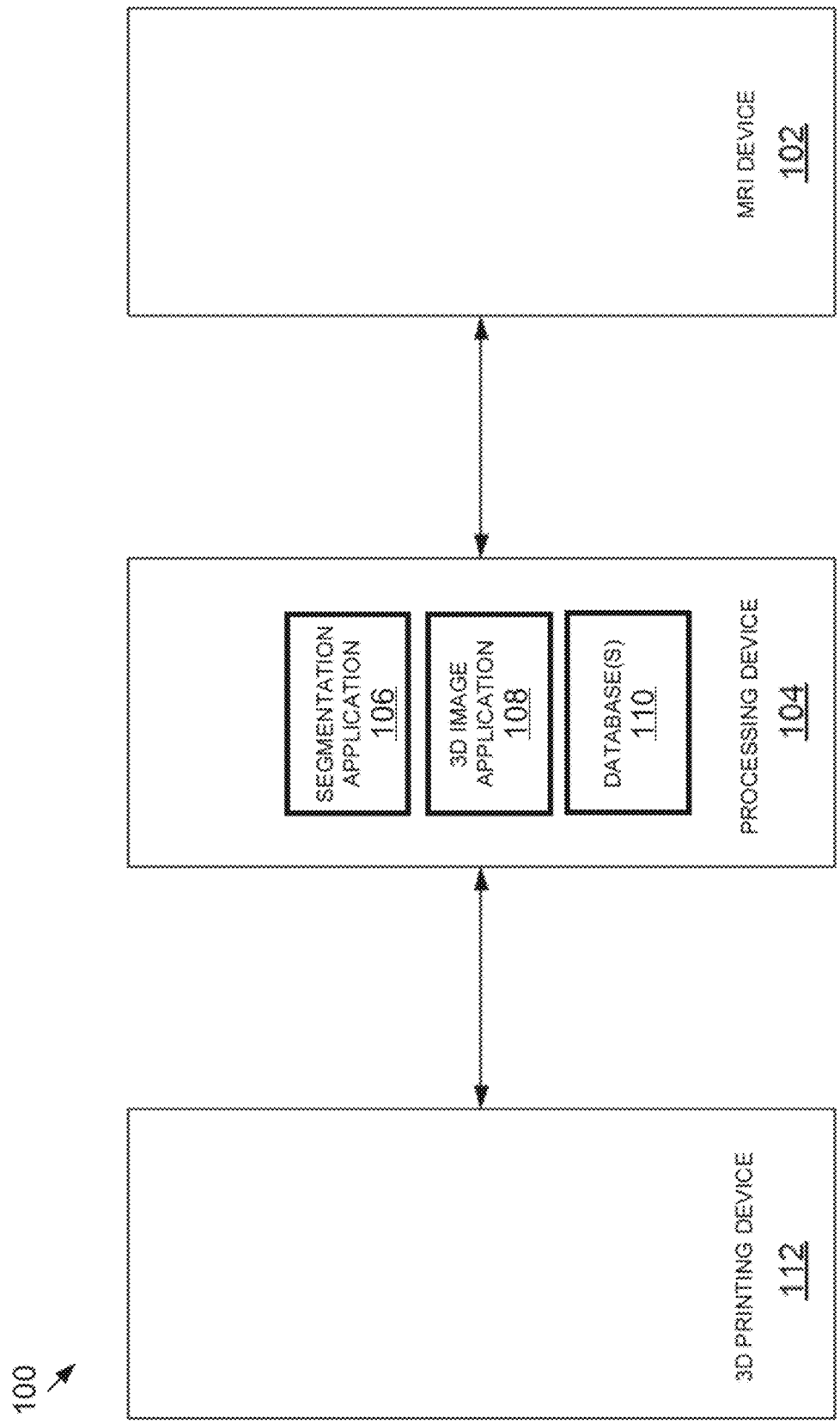
FIG. 1 depicts an exemplary 3D imaging and post-contrast brain lesion representation system according to an embodiment of the disclosure.

Referring now to the drawings, FIG. 1 depicts an exemplary 3D imaging and brain lesion or tumor representation system 100 according to an embodiment of the disclosure. In the embodiment shown, an MRI device 102 may be provided. The MRI device 102 may be a 3D MRI device, or one or more MRI devices providing both 2D and 3D imaging capabilities. A processing device 104 may be capable of receiving 3D images taken by the MRI device. Processing device 104 may be a part of a computer system that may include standard components such as a hard drive, monitor, printer, keyboard, and mouse, among others, that may enable a user to interact with the processing device 104. In the embodiment shown, processing device 104 may include one or more of a segmentation application 106, a 3D imaging application 108, and one or more databases 110. In some embodiments, segmentation application 106 may be configured to receive one or more MRI images from MRI device 102, segment the one or more MRI images into one or more regions, and enable a selection of one or more regions. These selected regions may be referred to as regions of interest (ROI). In some embodiments, the selection of ROI may be done automatically by processing device 104. In some embodiments, the selection of ROI may be done by a user.

In some embodiments, the selected ROI may be exported by segmentation application 106 and imported into 3D image application 108. In some embodiments, 3D image application 108 may generate one or more 3D maximum intensity projection (MIP) images of the selected ROI. In some embodiments, the selected ROI may correspond to one or more regions of contrast enhancement of a brain lesion or tumor. In some embodiments, the selected ROI may be converted to stereolithography (.stl) format and/or displayed as 3D orthographic images to enable orthographic views. The one or more 3D images may be displayed to a user and 3D image application 108 may enable a user to view and manipulate the one or more 3D images. In some embodiments, image manipulation capabilities may include capabilities to rotate, zoom, mark, color, and select the one or more images. In some embodiments, one or more databases 110 may contain information corresponding to various brain lesion characteristics and physiology. Examples of these brain lesion characteristics may include shape or geometric characteristics, size characteristics, topographical characteristics, volume characteristics, surface area characteristics and the like. In some embodiments, the brain lesion characteristics may be associated with one or more stratified categories of risk and/or treatment. Examples of these stratified categories may include characteristics that differentiate clinical stability versus disease advancement, characteristics that predict a more aggressive or less aggressive disease course, characteristics associated with varying degrees of injury, characteristics related to positive or negative treatment responses, characteristics that differentiate between disease types, and characteristics that differentiate disease advancement from treatment effects. In some embodiments, processing device 104 may be configured to send data corresponding to the one or more 3D images to a 3D printing device 112. 3D printing device 112 may create a 3D physical representation of the received one or more 3D images.

Figure 2:
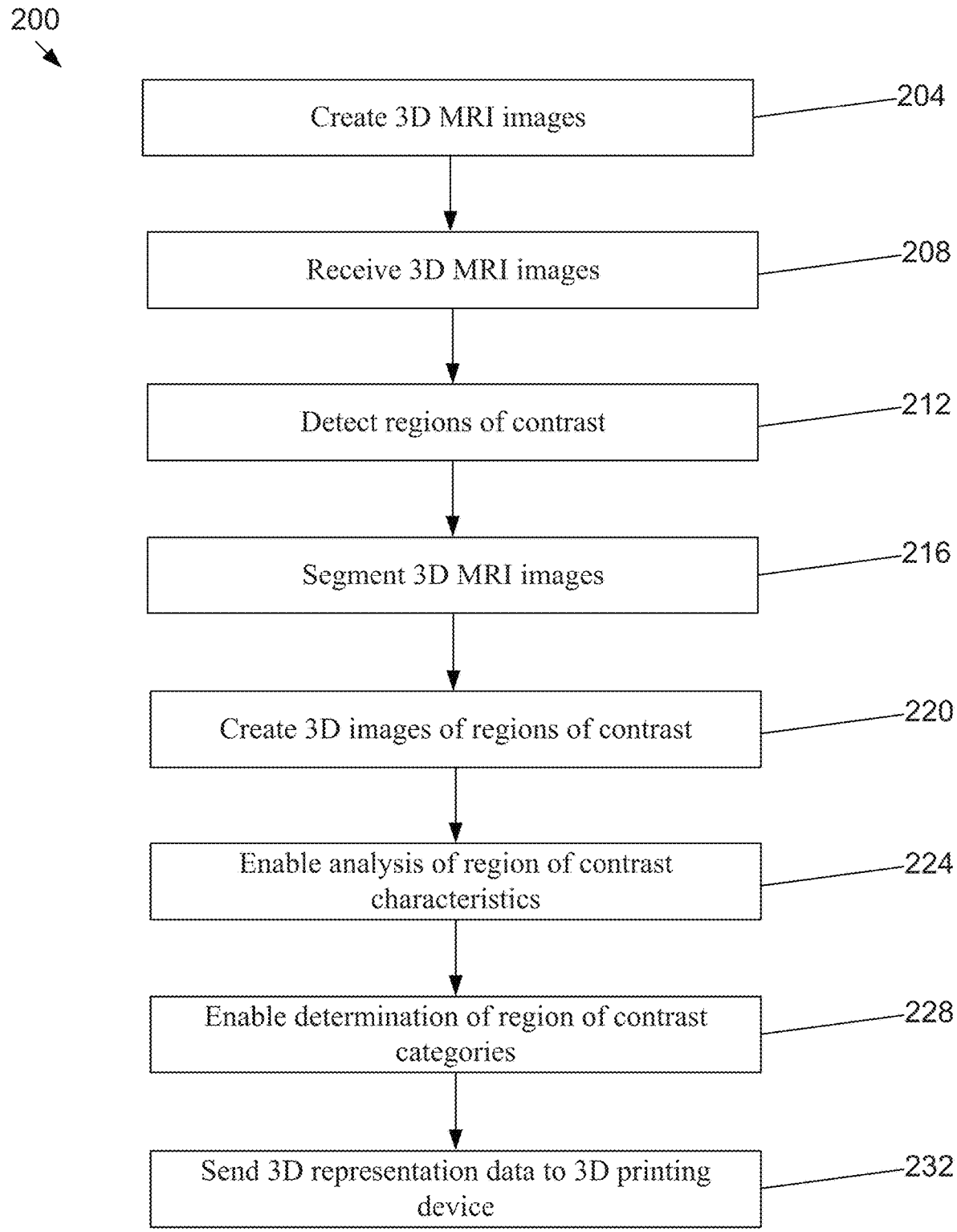
FIG. 2 depicts an exemplary method for creating 3D representations of post-contrast brain lesion characteristics according to an embodiment of the disclosure.

FIG. 2 depicts an exemplary method 200 for creating 3D representations of brain lesion/tumor ROI according to an embodiment of the disclosure. In one embodiment of the disclosure, method 200 may be implemented by system 100. In the embodiment shown in FIG. 2, method 200 may begin at step 204 by creating one or more 3D MRI images of a brain lesion. In some embodiments, the one or more 3D MRI images are created by receiving one or more 3D MRI images of a patient's brain, segmenting the one or more 3D MRI brain images into one or more ROI corresponding to a brain lesion/tumor, and creating a 3D MRI image of the ROI.

Method 200 may continue at step 208 by receiving the one or more 3D MRI images of the ROI corresponding to one or more isolated brain lesions/tumors. Method 200 may continue at step 212 by detecting one or more regions of contrast enhancement of the received one or more 3D MRI images of the isolated brain lesion. Before a patient receives the 3D MRI, the patient can be administered a contrast substance (e.g., gadolinium complexes, gadolinium compounds, a mixture including a dye/pigment) that will enter the bloodstream and travel to the brain lesion. In some embodiments, the contrast substance can be a paramagnetic agent. Once the contrast substance reaches the brain lesion, it may disperse at different concentrations into the various sections of the brain lesion based on the rate of growth, structural characteristics, and degree of blood brain barrier permeability of the brain lesion. For example, a higher concentration of the contrast substance may be drawn to an area of the brain lesion exhibiting a high growth rate, having a large number of blood vessels, or a weakened structural integrity. A lower concentration of the contrast substance may be drawn to an area of the brain lesion that is less physiologically active due to reduced tumor growth and/or reduced permeability of the blood brain barrier.

Method 200 may continue at step 216 by segmenting the received one or more 3D MRI images. In some embodiments, segmenting step 216 may include segmenting the one or more MRI images into the one or more regions of contrast enhancement. The one or more regions of contrast enhancement may correspond to different distinct sections of the one or more brain lesions. In some embodiments, regions of contrast enhancement may be selected in 3D format using an MIP 3D file. In this way, the computer system and/or a user may manipulate a 3D object in 2D space and may select one or more regions of contrast enhancement for further analysis. In another embodiment, regions of contrast enhancement may be automatically selected in 3D format from the 3D MRI images by the computer system and modified manually by the user. Isolating regions of contrast enhancement from 3D MRI images of brain lesions may allow for a better appreciation of brain lesion characteristics, risk factors associated with those characteristics, and possible treatments. In a 2D view, a variety of signals may influence pixel intensities that may result in pixel misclassification. As a result, creating 3D models from 2D ROI selections results in inaccurate representations. Isolating lesions from 3D images may overcome some of these shortcomings of 2D lesion isolation. In some embodiments, the different segments of the one or more MRI images may be displayed in different colors or display intensities.

Method 200 may continue at step 220 by creating one or more 3D images of isolated regions of contrast enhancement. In some embodiments, the one or more 3D images may be orthographic images or MIP images. In some embodiments, method 200 may continue at step 224 by enabling the analysis of one or more brain lesion or region of contrast enhancement characteristics. For example, a computer system may analyze the one or more images to determine one or more characteristics of the brain lesion and/or certain regions of contrast enhancement of the brain lesion. A user may also analyze the one or more images by interacting with the computer system. In some embodiments, metadata may be used to denote a type or category of a region of contrast enhancement characteristic. In some embodiments, region of contrast enhancement characteristics may include geometric characteristics. Geometric characteristics may provide insights into a size and shape of a brain lesion. Examples of geometric characteristics may include lesion symmetry/asymmetry, surface morphology (e.g., complex surface features), the existence of lobes and/or protrusions, and other shape characteristics (e.g., amorphous, ovoid). In some embodiments, region of contrast enhancement characteristics may include surface characteristics. Surface characteristics may provide insights into lesion surface traits and lesion properties not associated with geometry. Examples of surface characteristics may include differences in the contrast enhanced shell, the existence of surface microstructures, surface topography (e.g., steepness/sheerness of surface peaks and valleys), surface irregularities (e.g., fullness of the outer contrast enhanced shell, complex surface morphology), and a non-uniform distribution of mass of the lesion. In some embodiments, the computer system may engage in machine learning to generate descriptive surface, shape, and signal characteristics from the entire lesion or sections within lesions in order to more efficiently and accurately classify lesion types.

Method 200 may continue at step 228 by enabling a determination of a region of contrast enhancement category.

In some embodiments, a computer system may compare the one or more region of contrast enhancement characteristics to one or more previously stored region of contrast enhancement characteristics to determine possible matches. In some embodiments, one or more previously stored region of contrast enhancement characteristics may correspond to one or more region of contrast enhancement categories. In instances where the analyzed one or more region of contrast enhancement characteristics match one or more previously stored region of contrast enhancement characteristics, the computer system may determine one or more possible risk characteristics and/or treatment options of the one or more region of contrast enhancement. In some embodiments, a user may be able to determine one or more possible risk characteristics and/or treatment options of the one or more region of contrast enhancement based on each of their one or more region of contrast enhancement characteristics. In some embodiments, method 200 may continue at step 232 by sending data corresponding to the one or more 3D brain lesion images to a 3D printing device. Based on the received data, the 3D printing device may create a 3D physical representation or printed model of a region of contrast enhancement. In some embodiments, the 3D physical representation may exhibit one or more of the region of contrast enhancement characteristics. A user may use the 3D physical representation as an additional tool to help the user determine characteristics of the region of contrast enhancement of for patient or healthcare provider education.

Figures 3A, 3B, 3C:
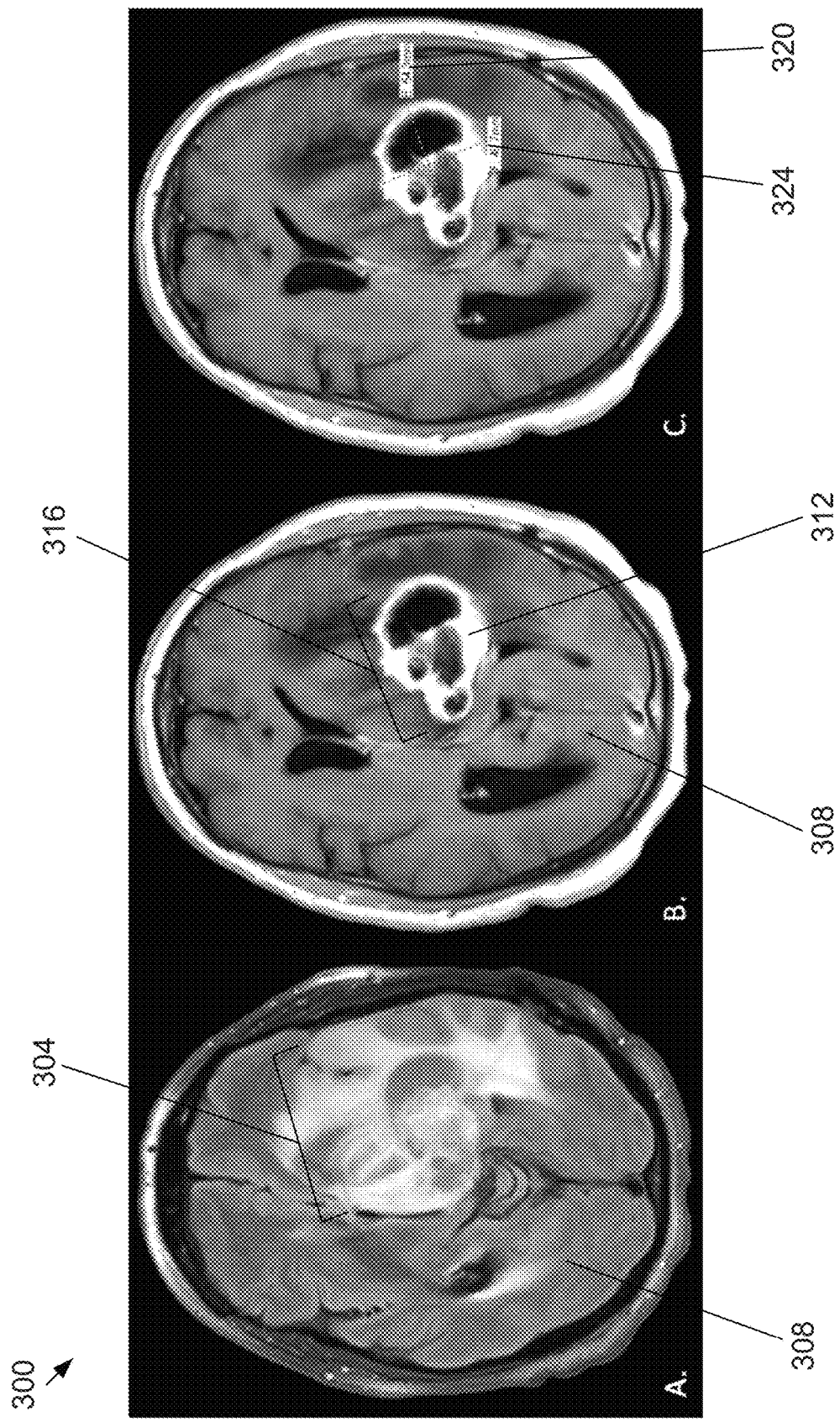
FIGS. 3A-C depict exemplary 2D MRI images showing an administration of a contrast substance into a patient brain and a post-contrast brain lesion.

FIGS. 3A-C depict exemplary 2D MRI images 300 that are currently used to detect and analyze brain lesion characteristics. 2D MRI images may provide multiple views from different imaging angles. For example, at least one sagittal image, at least one axial image, and at least one coronal image may be provided. In many traditional methods, 2D MRI images have been used to diagnose the existence of brain lesions and determine lesion characteristics. Before a patient receives the 2D MRI, the patient can be administered a contrast substance that will enter the bloodstream and travel to the brain lesion. As shown in FIG. 3A, a 2D MRI image depicts a brain lesion 304 (specifically, a glioblastoma tumor in this figure) prior to the administration of the contrast substance. The brain lesion 304 can be clearly distinguished from unaffected brain tissue 308 (shown in various shades of gray and black). Eventually, as shown in FIG. 3B, the contrast substance 312 (shown as a bright, white substance) is able to leak out of a blood vessel in a specific part(s) of the brain lesion 304 and collects in different concentrations in different areas of the brain lesion 304. In this way, the contrast substance 312 clearly delineates specific boundaries of certain regions of contrast enhancement 316 of the brain lesion 304 from other portions of the brain lesion and unaffected brain tissue 308. Once the regions of contrast enhancement 316 of the brain lesion 304 are isolated from the other portions of the brain lesion and unaffected brain tissue 308 in the 2D MRI image, certain characteristics of the brain lesion can be determined, such as brain lesion dimensions (e.g., length 320 and width 324), as shown in FIG. 3C. However, the analysis that can be performed on the brain lesion using such 2D MRI images is limited.

Figure 4A:
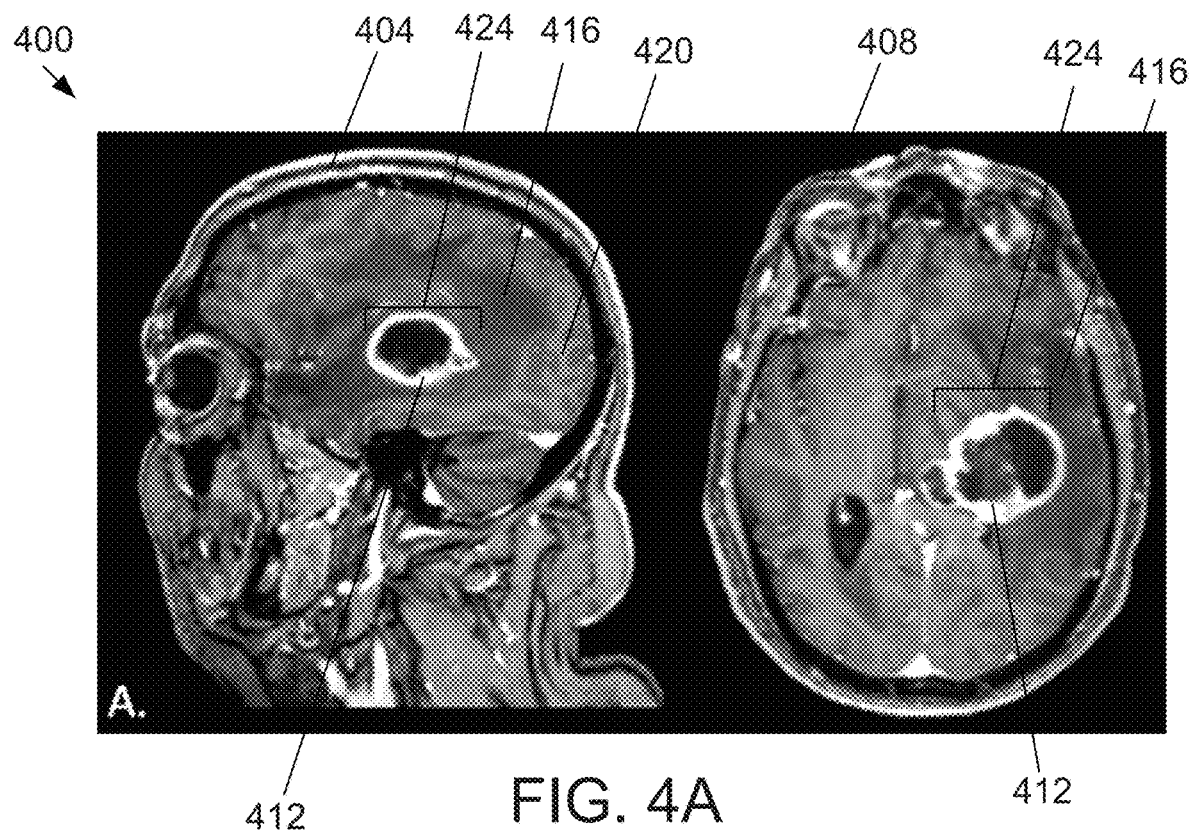
FIGS. 4A-B depict exemplary 2D MRI images showing an administration of a contrast substance into a patient brain and a post-contrast brain lesion according to an embodiment of the disclosure.
Figure 4B:
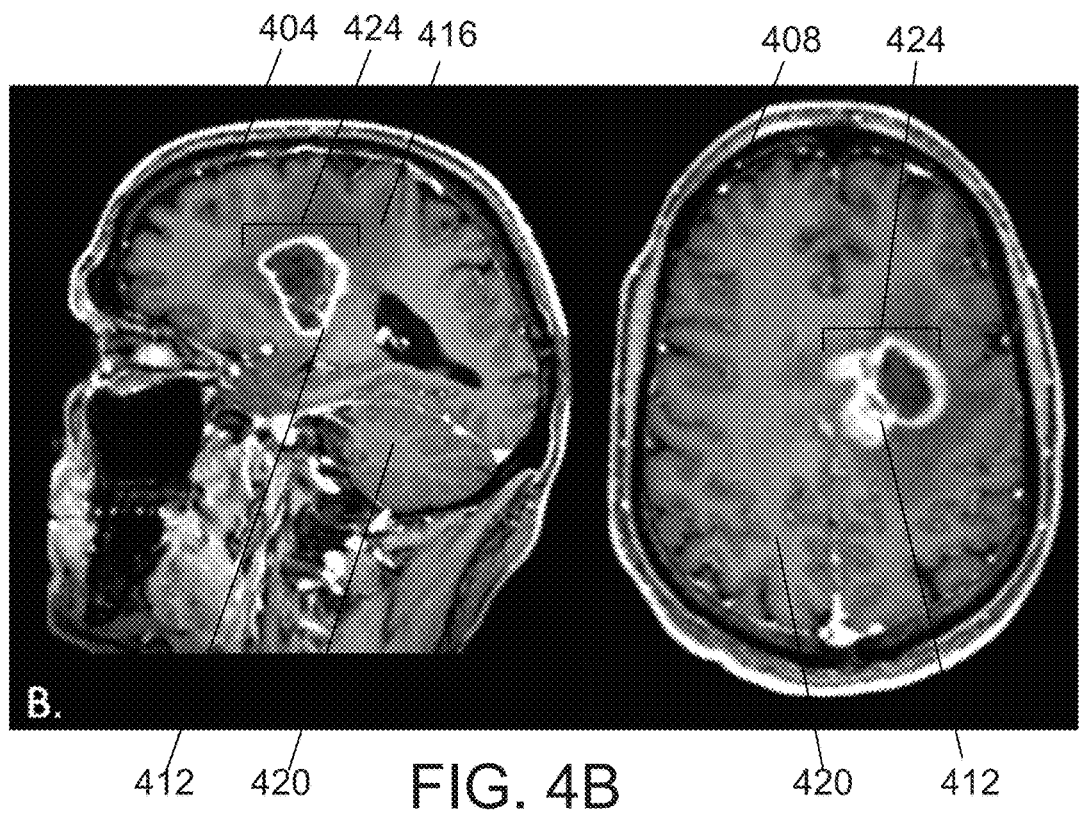

As such, in the disclosed embodiments, one or more MRI images 400 from a 3D series may be received by a computing system from an MRI system having 3D imaging capabilities, as shown in FIGS. 4A-B. In the embodiment shown, sagittal images 404 and axial images 408 are shown. Similar to the images shown in FIGS. 3A-C, the MRI images 400 illustrate the contrast substance 412 (depicted in one or more shades of white) as contrasted with non-contrast enhancing brain lesion tissue 416 and healthy brain tissue 420 (depicted in one or more shades of gray). As shown, the contrast substance 412 clearly delineates the boundaries of certain regions of contrast enhancement of the brain lesion 424 from non-contrast enhancing portions of the brain lesion 416 and from healthy portions of the brain tissue 420. This may assist a user viewing the image to distinguish regions of contrast enhancement of brain lesions from other brain lesion areas and from healthy brain tissue. In some embodiments, 3D MRI images may be configured to be accessed and/or manipulated by a user. In some embodiments, the user may be able to rotate, zoom, mark, color, and select areas of the 3D MRI images. In some embodiments, a computer system may perform a segmentation process on 3D MRI images that may segment the 3D MRI images into one or more ROI representing a brain lesion. A brain lesion may be selected by the computer system or the user and may be denoted or saved as a ROI.

Figure 5A:
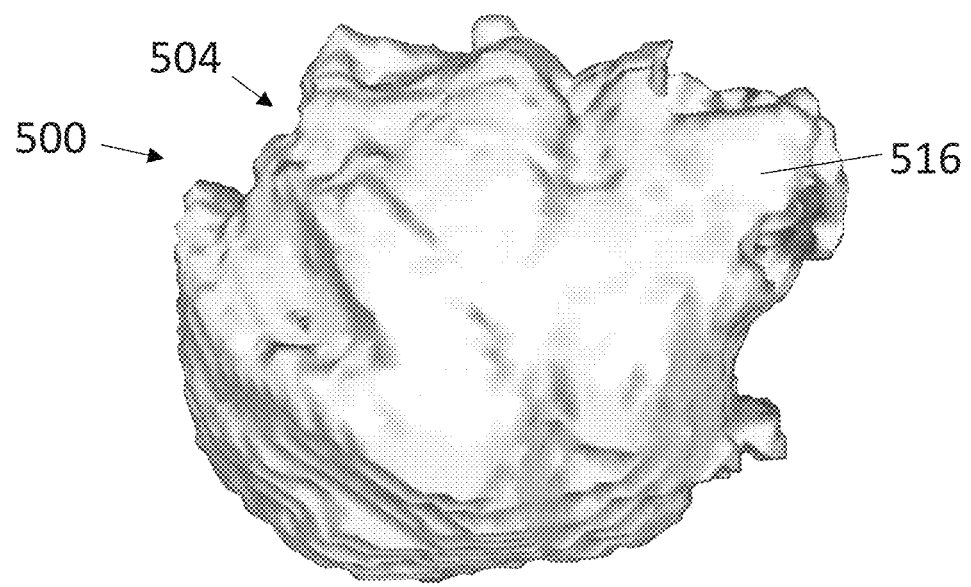
FIGS. 5A-B depict exemplary 3D brain lesion images that may be constructed of the brain lesions shown in FIGS. 4A-B according to an embodiment of the disclosure.
Figure 5B:
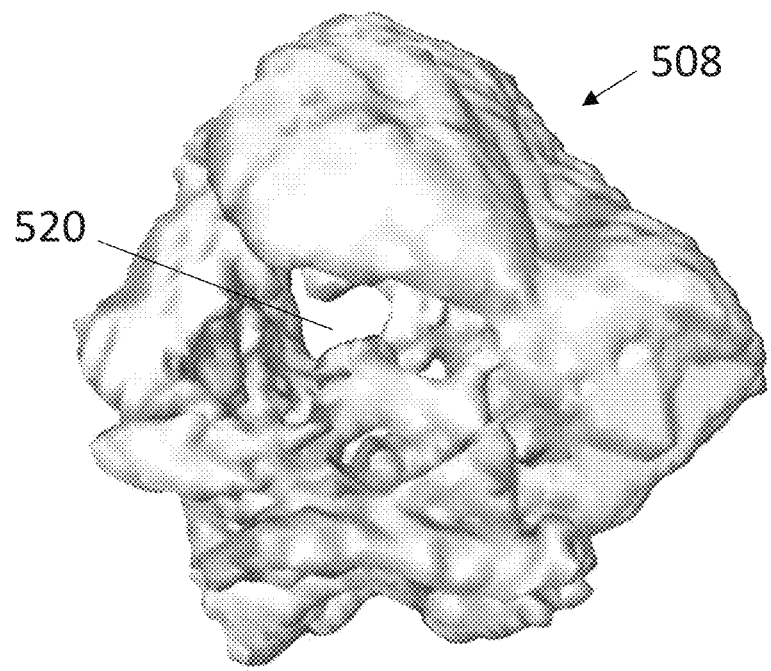

FIGS. 5A-B depict exemplary 3D brain lesion images 500 that may be constructed according to an embodiment of the disclosure. In the embodiment shown, the 3D brain lesion image 504 shown in FIG. 5A corresponds to the brain lesion shown in the ROI of FIG. 4A and the 3D brain lesion image 508 shown in FIG. 5B corresponds to the brain lesion shown in the ROI of FIG. 4B. In the embodiment shown, 3D brain lesion images 500 may depict a brain lesion 512 and one or more brain lesion characteristics, such as a round protuberance 516 existing on a particular surface of the brain lesion or a hole 520 disposed through the mass of the brain lesion. In some embodiments, 3D brain lesion images 500 may be an MIP image. In some embodiments, 3D brain lesion images 500 may be an orthogonal image generated from one or more selected ROI that provides orthogonal views to a user. 3D brain lesion images 500 may also be in stereolithography format. In some embodiments, 3D brain lesion images 500 may provide a 3D spatial visualization of the brain legion and may be configured to be accessed and/or manipulated by a user. In some embodiments, the user may be able to rotate, zoom, mark, color, and select areas of the 3D brain lesion images 500. As discussed above, one or more brain lesion characteristics may be displayed. In some embodiments, data related to lesion characteristics such as shape, size (e.g., x, y, and z planes), volume, surface area, surface area to volume ratio, volume to surface area ratio, topographical surface characteristics, geometric characteristics, thickness of the contrast enhanced shell, and the like may be acquired from the 3D MRI images 400 by the computer system in order to depict the brain lesions 504, 508 and their brain lesion characteristics as accurately as possible. Due to the accuracy of the 3D brain lesion images 500, the computer system and/or the user may more efficiently and accurately determine characteristics of the brain lesion that may be significant in determining categories of risk and treatment of the brain lesion.

Figure 6A:
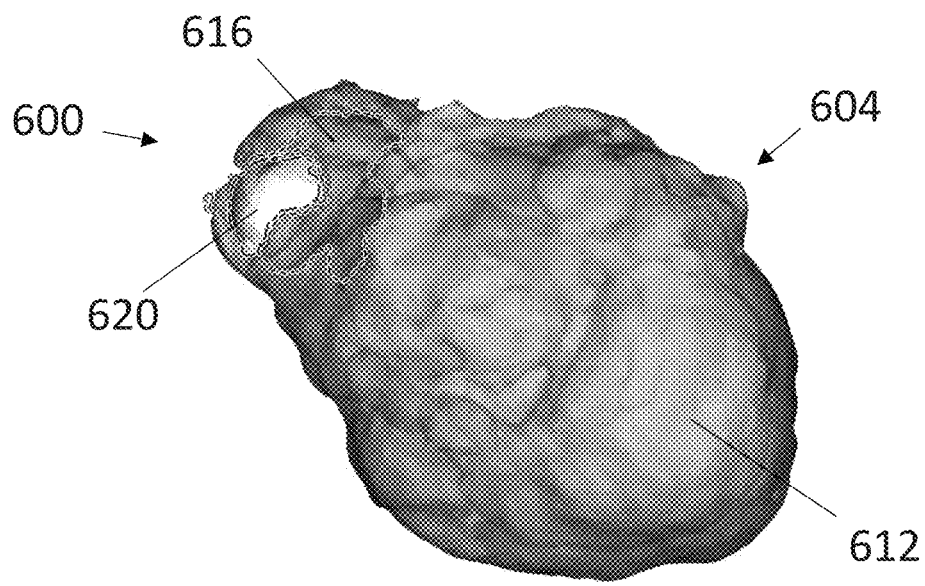
FIGS. 6A-B depict exemplary 3D post-contrast brain lesion images that may be constructed of the brain lesions shown in FIGS. 5A-B according to an embodiment of the disclosure.
Figure 6B:
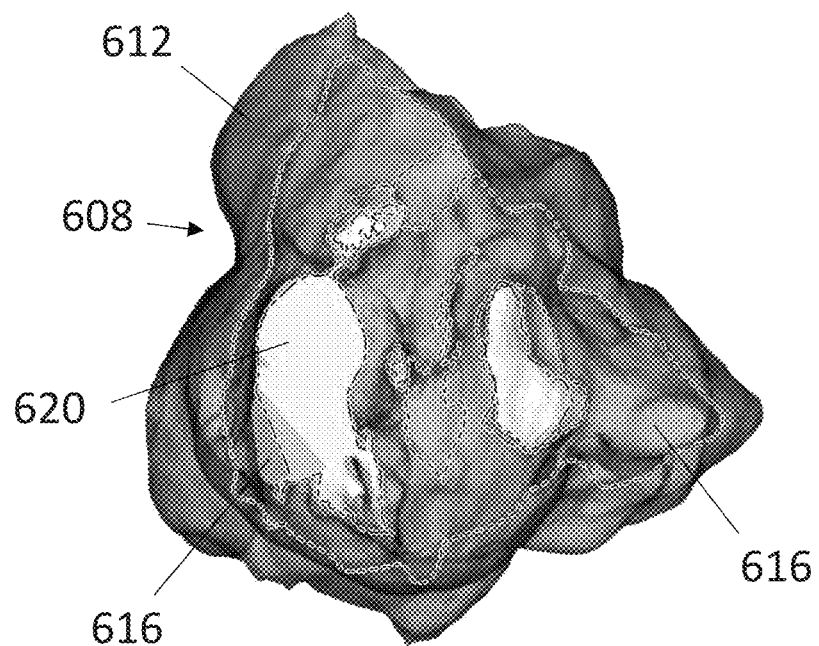

FIGS. 6A-B depict exemplary 3D brain lesion images 600 showing various regions of contrast of the depicted post-contrast brain lesions according to an embodiment of the disclosure. In the embodiment shown, the 3D brain lesion image 604 shown in FIG. 6A corresponds to the 3D brain lesion image 504 shown in FIG. 5A and the 3D brain lesion image 608 shown in FIG. 6B corresponds to the 3D brain lesion image 508 shown in FIG. 5B. In the embodiment shown, different areas of contrast may be illustrated by different colors and/or intensities. For example, in the 3D brain lesion image 604 of FIG. 6A, one region of contrast 612 (falling outside of the dashed and dash-dotted lines)

corresponds to an outer shell of the contrast enhanced lesion and may be represented in a red color. A region of contrast 616 (bounded by the dashed line) that corresponds to the inner region of the contrast enhanced lesion may be represented in an orange color, and a region of contrast 620 (bounded by the dash-dotted line) that corresponds to a hole in the outer shell may be represented by a blue color. In the exemplary 3D brain lesion image 608 of FIG. 6B, the region of contrast 612 (falling outside of the outermost dashed line) representing the outer shell of the contrast enhanced lesion may be represented by a red color. Regions of contrast 616 (falling between the outermost dashed line and the dash-dotted lines) representing other surface areas of the lesion may be represented by an orange and/or yellow color, indicating the inner region of the contrast enhanced lesion. Multiple regions of contrast 620 (falling within the dash-dotted lines) of the lesion may be represented by a blue color, indicating that the lesion has more holes or imperfections by the outer shell than the lesion shown in FIG. 6A. Regions of contrast 616 represent areas within the inner region of the contrast enhanced lesion. By representing different regions of contrast with different colors and intensities (and/or other visually-distinguishable parameters), the computer system and/or a user viewing the 3D brain lesion images can determine important characteristics about the lesion that may be correlated with growth areas or regions of recovery, treatment response, and risk factors of the lesion.

FIGS. 7A-8C depict exemplary experimental results from implementations of the systems and methods described by the embodiments of the disclosure. In order to test the disclosed embodiments, a series of tests were performed on a group of recruited patients. The inclusion criteria for patient selection was: i) male or female patients >18 years of age with, ii) a confirmed diagnosis of GBM by histopathology consistent with WHO grade IV established criteria, and iii) recent brain MRI within the past 60 days demonstrating gadolinium enhancement. Exclusion criteria included: i) pregnant women, ii) prior or current exposure to bevacizumab, iii) previous allergic, anaphylactoid, or intolerance to gadolinium-based contrast agents, iv) estimated glomerular filtration rate (eGFR) of <30 mL/min/1.73 m$^2$), and/or v) contraindications to MRI.

The recruited patients with a confirmed diagnosis of GBM were placed into two groups. The patients in one group were clinically stable patients without new or worsening neurological symptoms with clinical state verified by a board certified neuro-oncologist. The patients in the other group exhibited new or worsening neurological symptoms unattenuated by glucocorticosteroid increase whose combined symptoms and radiologic changes on MRI warranted a change to their established treatment plan due to probable clinical progression in congruence with established Response Assessment in Neuro-Oncology (RANO) response criteria for progressive disease.

Standardized brain MRI studies were performed on all study participants and all analyses implemented without knowledge of clinical history, current or past treatments, or disease duration. All imaging studies were performed on a 3T MRI scanner using a 32-channel phased array coil for reception and body coil for transmission. Gadobutrol 0.1 ml/kg was administered at a rate of 2cc/second. A five-minute delay was performed prior to the acquisition of post-contrast sequence data. Each MRI study included one or more scout localizers, pre- and post-contrast 3D high-resolution inversion recovery spoiled gradient-echo T1-weighted isotropic (1.0×1.0×1.0 mm$^3$, TE/TR/TI-3.7/8.1/864 ms, flip angle 12 degrees, 256×220×170 mm$^3$ FOV, number of excitations (NEX)=1, 170 slices, duration: 4:11 min), a 3D fluid-attenuated inversion recovery (FLAIR) (1.1×1.1×1.1 mm$^3$, TE/TR/TI=350/4800/1600 ms, flip angle 90 degrees, 250×250×180 mm$^3$ FOV, NEX=1, 163 slices, duration: 5:02 min), and 3D T2 sequence acquired in sagittal plane (1.0×1.0×1.0 mm$^3$, TE/TR/TI=229/2500/1600 ms, flip angle 90 degrees, 250×250×180 mm$^3$ FOV, NEX=1, 164 slices, duration: 4:33 min). However, other types of MRI scanners and other 3D MRI imaging study parameters may be used, such as anisotropic protocols. Examples of these MRI images are image 704 shown in FIG. 7A and image 804 shown in FIG. 8A. The contrast substance 708, 808 (shown as a bright, white substance) can be clearly distinguished from unaffected brain tissue 712, 812 (shown in various shades of gray and black).

In the embodiments shown, post-contrast enhanced tumor image segmentation of the MRI images was performed using segmentation software (e.g., aySegmentation v1.00.004 plug-in of aycan OsiriX® PRO v3.00.008). However, other types and/or methods of image segmentation may be used. During segmentation, focal brain tumors were verified from simultaneously viewed 3D high-resolution pre- and post-contrast T1-weighted sequences in axial, coronal, and sagittal view. The contrast enhancing region and hypointense necrotic center of each tumor were selected manually using a segmentation tool, and segmented lesions were saved as specified regions of interest (ROI). All selected ROI files were exported into stereolithography (.stl) format, visually evaluated using 3D software (e.g., Mesh-Lab, Visual Computing Lab—ISTI—CNR, v1.3.3), and exported for statistical analysis to a computing/processing system. One or more 3D image files were generated using the 3D isolation software, allowing for 3D spatial visualization of the brain and lesions of the selected ROI. However, other types and/or methods of 3D image creation may be used. Examples of these 3D lesion images are images 716 shown in FIG. 7B and image 816 shown in FIG. 8B.

In some embodiments, identified post-contrast lesions depicted by the 3D images can be printed using a 3D printing device (e.g., MakerBot® Replicator 2× Experimental 3D unit with 1.75 mm acrylonitrile butadiene styrene (ABS) filament with a build platform temperature of 110° F and an extruder temperature of 230° F.). Using fused filament fabrication, a 200 µm layer resolution can be achieved with the printed files. Individual lesions can be printed at actual size and also enlarged based on user preference. However, other types of 3D printers and/or other types of 3D printing technologies may be used to create 3D printed molds of the identified post-contrast lesions. Other degrees of resolution may also be achieved.

Figure 7D:
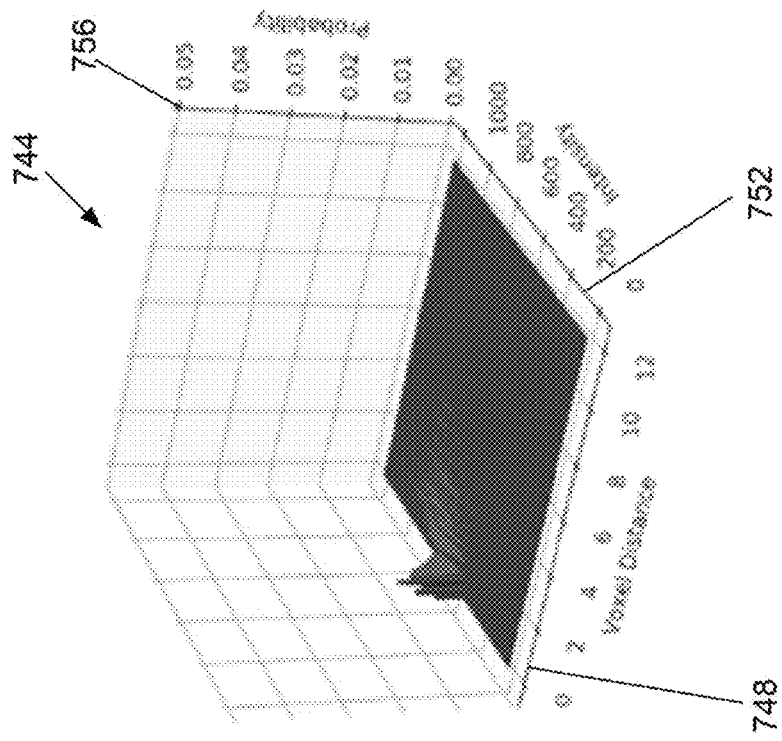
Figure 7C:
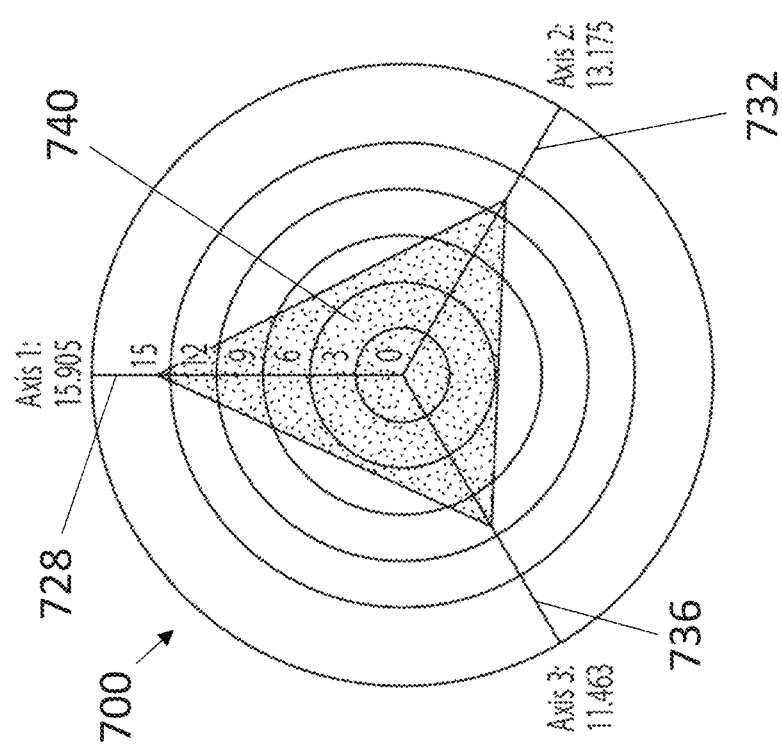
Figures 8A, 8B:
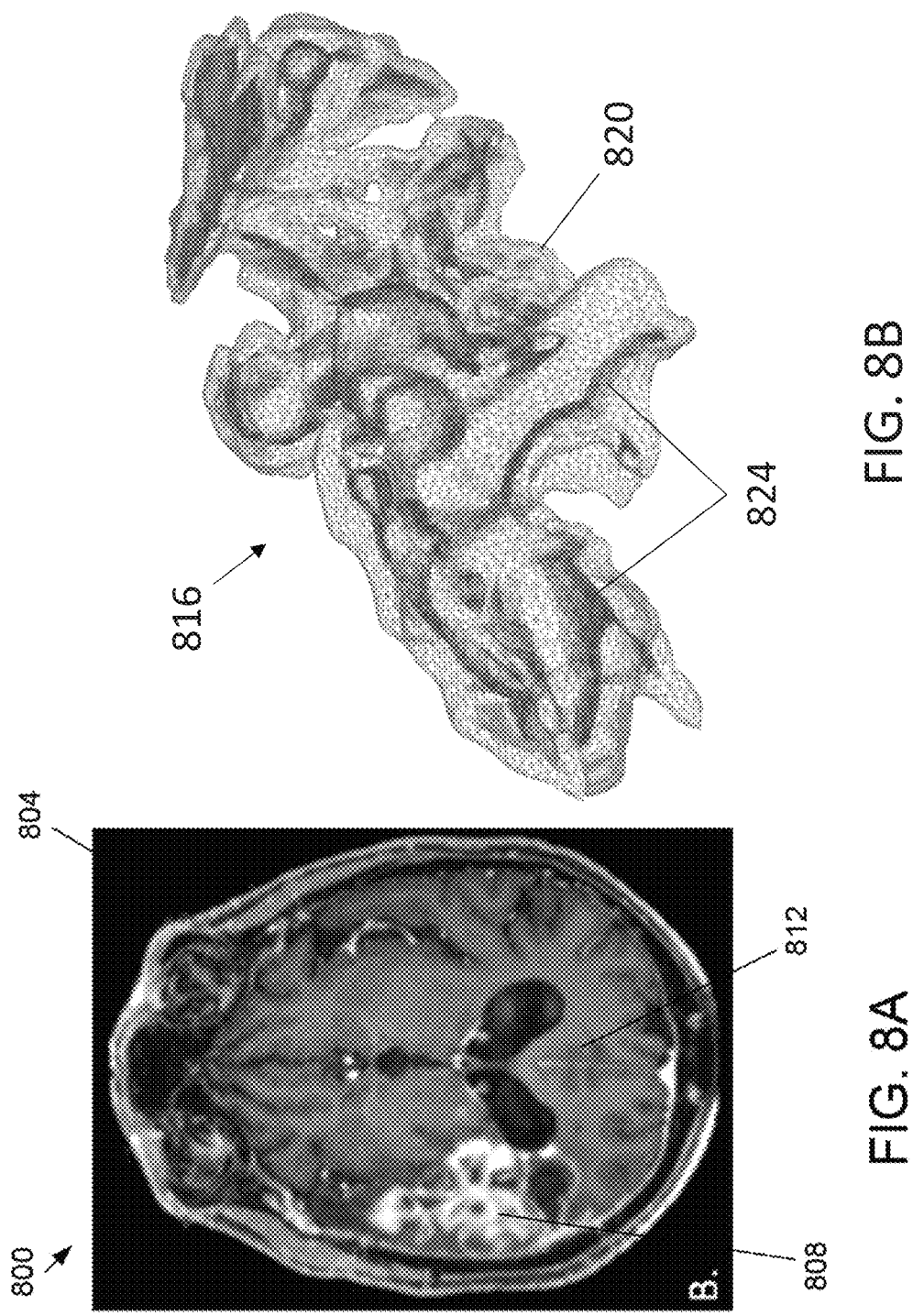
FIGS. 8A-D depict exemplary experimental analysis results from an implementation of the systems and methods described by an embodiment of the disclosure.
Figure 8D:
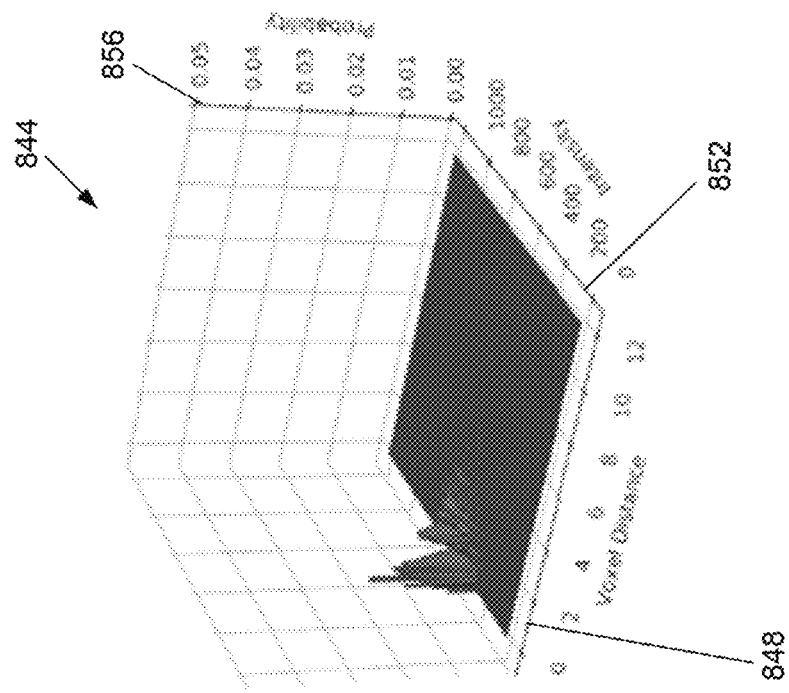
Figure 8C:
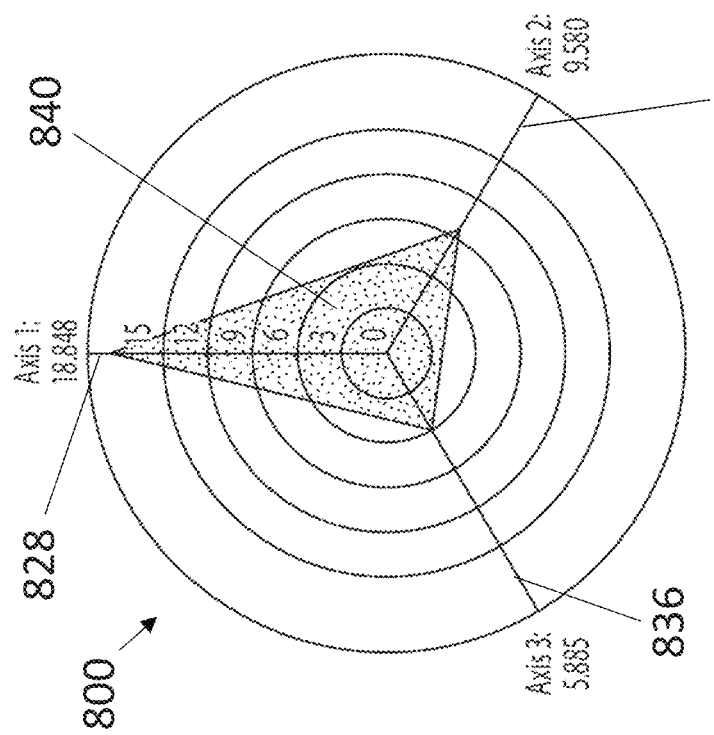

As shown in FIGS. 7B and 8B, the 3D lesion images 716, 816, are isolated into various regions of contrast enhancement designated by different color shades. For example, in images 716, 816, a region of contrast enhancement 720, 820 representing an outer shell of the tumor can be shown in a white color (in the figures, light grey). Similarly, a region of contrast enhancement 724, 824 representing the inner aspect of the contrast enhanced lesion can be shown in a pink and/or purple color (in the figures, darker greys). In the embodiments shown, the segmented contrast enhancing outer shell (represented by region of contrast enhancement 720, 820) of each tumor was analyzed using principal component analysis (PCA). The input data (X), representing all 3D vertices on the segmented shell surface, was represented as a matrix (M) such that M=XX$^T$ after zero-centering. The singular value decomposition (SVD) for M was calculated to find the highest kth eigenvalue and eigenvector. Three eigenvector outputs for each tumor were acquired, representing the three orthogonal axes (e.g., axes 728, 732, 736 in FIG. 7C and axes 828, 832, 836 in FIG. 8C, respectively), which maximize variance by projection. As shown in FIGS. 7C and 8C, the three eigenvector outputs were analyzed as triangles 740, 840 in 3D space normalized to an equilateral triangle, and the shape variance of each tumor was computed. After rejecting equal variance based on Bartlett's test, a two-sample t-test assuming unequal variance was used to determine the significance of the difference between the variance of the two independent samples.

In the embodiments shown in FIGS. 7C and 8C, a medial axis transformation (MAT), which is a fundamental shape descriptor, was used to represent the "skeleton" of the post-contrast enhanced lesion. For every point on the medial axis, the distance to at least two closest points on the lesion surface was stored as the radius of the corresponding circle that occupied the space between the inner and outer boundaries of the contrast enhancing shell surface. The Q-MAT (quadratic medial axis transformation) method was used for quadratic error minimization to compute a compact representation of the MAT that remained geometrically accurate, as well as remove insignificant, unstable branches to produce a piecewise linear approximation of the MAT data. The Q-MAT was used to extract the medial axis vertices of the segmented contrast enhancing shell of the tumor and reduced the number of vertices by a ratio of 0.05 with respect to the number of original MAT vertices. In the embodiments shown in FIGS. 7C and 8C, a histogram of the MAT vertices was created to show the distribution of the MAT vertices along each radius, corresponding to the 3D shell thickness of each tumor. The mean and variance of the radii were analyzed between the two clinical states using a two-sample t-test after verifying normality of the two samples using a QQ-plot and verifying equality of variance among the two samples using Bartlett's test.

The distance of each 3D voxel in the contrast enhancing region to the nearest 3D surface mesh was calculated using a distance transform. Three different distances were calculated per voxel corresponding with the distance to three distinct surface meshes: i) the outside surface representing the outer shell of the contrast enhancing region, ii) the inner surface defined as the surface of the non-contrast enhancing region within the contrast enhancing shell, and iii) the nearest distance to either the outer or inner surface. In the embodiments shown in FIGS. 7D and 8D, a 3D distance transform and intensity histogram 744, 844 was then created with the X axis 748, 848 representing the distance transform value, the Y axis 752, 852 representing the intensity value, and the Z axis 756, 856 representing the number of voxels in each transform distance and intensity grid, respectively. The mean vector of the standard deviation of the distance and the standard deviation of the intensity were compared between the progressive and stable groups using Hotelling's T2 after verifying the assumptions of multivariate normality using Royston's Test and equality of covariance matrices using Box's Test. The mean vector of the average distance and the average intensity were compared between the progressive and stable groups using a modified version Hotelling's T2 to account for evidence of unequal covariance matrices based on Box's test after verifying the assumptions of multivariate normality using Royston's Test.

As shown in FIGS. 6A and 6B, an isolated ROI was segmented into two parts: contrast enhancing and non-contrast enhancing regions representing the outer and inner surfaces, respectively. The inner surface was further divided into two sections: i) the area covered by the outer shell, and ii) the uncovered area, corresponding to a perforation in the 3D view of the outer surface shell. To compute these two areas, the non-contrast enhancing region was first analyzed by computing a normal for every triangular face on its surface mesh. A ray extending from the center of each triangular face in the direction of its surface normal was projected, allowing for an assessment of intersections within the mesh of the outside contrast enhancing region. A triangular area was identified as an uncovered region and added to the total uncovered area, if the ray failed to intersect with the outside mesh. A coverage ratio representing the amount of perforations in the contrast enhanced shell surface was calculated by dividing the total outside region area by the sum of the total outside region area and the total uncovered area of the inside region.

The performance of the presence of incomplete coverage of the contrast enhanced surface in predicting the clinical state was evaluated using true positives (near complete coverage of the contrast enhanced surface in a patient with clinical worsening), false positives (near complete coverage of the contrast enhanced surface in clinically stable patients), true negatives (incomplete coverage of the contrast enhanced surface in clinically stable patients), and false negatives (incomplete coverage of the contrast enhanced surface in patients with clinical worsening) to determine sensitivity, specificity, and positive predictive values with 95% confidence intervals (CI). A 2-tailed Fisher's exact test was used for analysis of the contingency tables. A p value≤0.05 was considered significant for all statistical tests performed.

The study cohort was comprised of 15 GBM patients (male: 11 (73%); median age (range): 62 years (36-72)) with a median disease duration of 6 months (range: 2-24 months). Hypermethylation of MGMT was present in 5 patients (33.3%) and wild type IDH1 mutations identified in 10 (66.7%). The majority of patients (80%) received concurrent treatment with temozolamide and chemoradiation. When comparing the demographic and clinical characteristics of the study cohort, the only significant difference between groups involved treatment history. The baseline demographic and clinical characteristics of the entire study cohort and by clinical state are summarized in TABLE 1, shown below:

TABLE 1

Demographic and clinical characteristic data of the study cohort.

| | |
|---|---|
| Total (n) | 15 |
| Age, median years (range) | 62 (36-72) |
| Sex | |
| male, n (%) | 11 (73) |
| female, n (%) | 4 (27) |
| Ethnicity | |
| Hispanic, n (%) | 1 (7) |
| Non-Hispanic, n (%) | 14 (93) |
| Disease Duration, median months (range) | 6 (2-24) |
| Promoter of MGMT[1] | |
| unmethylated, n (%) | 5 (33.3) |
| methylated, n (%) | 1 (6.7) |
| unknown, n (%) | 9 (60) |
| IDH1[2] Mutation | |
| wildtype, n (%) | 10 (66.7) |
| mutated, n (%) | 1 (6.7) |
| unknown, n (%) | 4 (26.7) |

TABLE 1-continued

Demographic and clinical characteristic data of the study cohort.

Concurrent Chemotherapy with

| | |
|---|---|
| Chemoradiation temozolamide, n (%) | 12 (80) |
| Other, n (%) | 3 (20) |
| Time since last radiation treatment at 3D scan, median months (range) | 4 (0.53-19) |

[1] $O^6$-methylguanine-DNA-methyltransferase
[2] Isocitrate dehydrogenase 1

An analysis of potential deviations in shape between clinical groups was performed by studying the 3D contrast enhancing outer shell of all tumors. Results from the PCA data, normalized to exclude the impact of size, revealed distinct morphological variances between groups (p=0.005) with more non-spherical, asymmetric shapes identified in the group that was clinically stable (% (88%)). Lower orthogonal axis distance variances of 4.77-10.70 associated with greater shape symmetry, encompassed all patients with clinical progression along with a single clinically stable patient. Overall, the acquired 3D data provided more information than conventional 2D information and distinct spherical shapes exhibiting symmetry were appreciated in those subjects with reduced clinical stability (as shown, for example, in the shapes of the 3D lesion images of FIGS. 5A, 6A, and 7B) as compared to those who were more clinically stable (as shown, for example, in the shapes of the 3D lesion images of FIGS. 5B, 6B, and 8B).

Medial axis transformation data aimed at evaluating the uniformity of the radial distances, indicating shell width, revealed more dynamic isosurface differences in patients with clinical progression. For those patients who were clinically stable, higher probability values for smaller radii distances were observed, suggesting greater consistency in the thickness and an overall thinner contrast enhancing shell. However, analyzing the mean and variance of the MAT radii of the two clinical states demonstrated no significant difference between groups (p=0.38 and p=0.13 respectively).

By analyzing the relationship between the outer and inner shell surface areas, percent coverage data was computed to represent the fullness of the outer shell with lower values below 1.0 being associated with a greater amount of perforations within the shell. All patients with clinical progression were found to have coverage ratios >0.951. The predictive value of a post-contrast enhanced shell that was more uniformly full to clinical progression was determined with a sensitivity of 66.7% (95% CI 29.9-92.5), specificity of 100% (54.1-100), and PPV of 100% (p=0.028, 2-tailed Fisher's exact test) (as shown in the shape of the 3D lesion image of FIG. 6A).

The intensity of each voxel in the contrast enhancing region was analyzed in relation to the distance of that voxel from both the outer and inner surfaces and 3D histograms were created to visualize the data. Qualitative differences were not observed when comparing the histogram data. In addition, an evaluation of the mean and variance data regarding the degree of contrast enhancement by distance and the observed intensity did not reveal significant differences between groups (p=0.36 and p=0.32, respectively). When looking at the mean intensities between clinical groups alone, results trended more towards significance (p=0.10).

The effective management of patients with GBM requires an evaluation of clinical and neuroradiological data and the timely administration of available treatments. Differentiating the impact of therapeutic effects (i.e. tumor resection, chemoradiation, anti-neoplastic agents) and the innate immune response following such interventions from tumor progression based on alterations in acute blood brain barrier physiology may be difficult to determine, requiring additional time for declaration of disease advancement to be apparent before a change in treatment is made.

The 3D radiological characteristics corresponding with disease progression identified within the most physiologically active area of the tumor are consistent with the known pathophysiology of GBM. As GBM tumor cells in the absence of an applied stimulus are able to effectively deform their cellular shape to migrate outwards, uniform dispersion would be expected, resulting in 3D post contrast features to be more spherical in shape and the outer shell of the enhanced region to be fuller with reduced perforations. In contrast, the physiological response in neurologically stable patients would be expected to be more tailored to specific areas of increased inflammation when tumor growth is limited by prescribed treatments. The corresponding structure would be expected to be more non-spherical and elongated in shape with a decreased propensity for circumferential fullness, and a more disconnected 3D radiological pattern.

Analysis of the thickness of the contrast enhanced shell, the 3D reflection of the 2D width of the affected tissue, demonstrated no significant difference between the defined groups. This observation may be related to the reduced number of subjects studied and a true association may ultimately exist. The current data suggest that post-contrast radiological changes may not be indicative of disease progression. However, when observed in clinical practice or described within formal MRI reports, this feature commonly represents a key inflection point in patient management. Of note, the growth of the non-contrast enhancing necrotic center of GBM tumors was found to be faster relative to the growth of the contrast enhancing ring. Therefore, it is plausible that the 3D width of the contrast enhancing region would remain constant despite tumor progression.

The value of signal intensity data, acquired from different imaging sequences on MRI, has been extensively explored in relation to high grade gliomas. Ring enhancing gliomas on T1 post-contrast sequences were often found to have a corresponding mixed signal intensity centrally with a hypointense peripheral arc on T2 weighted imaging, differentiating high grade gliomas from other ring enhancing tumor types. In relation to assessing tumor recurrence, a general increase in intensity heterogeneity obtained from T2-weighted sequences was found to differentiate progression from pseudoprogression in GBM patients. Similarly, an increase in FLAIR signal intensity within the resection cavity post grand total resection (GTR) or subtotal resection (STR) normalized to the intensity of CSF correlated with tumor recurrence in high grade gliomas. In contrast, decreased FLAIR signal intensity within the peritumoral region post-resection predicted future progression of the infiltrative disease, and the amount of signal intensity reduction was found to be directly proportional to the likelihood of tumor recurrence. Signal intensity differences specifically focused on 3D T1 post-contrast data from GBM patients have not been previously described. After analyzing the acquired intensity data in relation to distance and relative frequency, no significant differences between clinical states were found. However, when evaluating the intensity frequencies alone between groups, there appeared to be a trend towards significance with greater mean intensity values seen in neurologically unstable patients.

By implementing this disclosed systems and methods, the application of 3D technology with post-contrast imaging data may inform healthcare providers with new insights into disease states based on spatial, surface, and structural patterns, extending beyond constrained 2D views, that may allow for surveillance approaches to evolve and for treatment transitions to occur more quickly. The disclosed systems and methods may also be used to assess for approved or research based treatments and for predicting future disease activity and clinical outcomes.

3D imaging capabilities provided by the present systems and methods may allow for tracking of tumor behavior (e.g., distinguishing tumor progression and pseudoprogression, assessing tumor response to therapy, and/or the like), shed light on the reasons for such behavior, and/or predict such behavior, to an extent that is not provided by, or is not readily appreciable from, conventional review of 2D MRI images.

Figure 9:
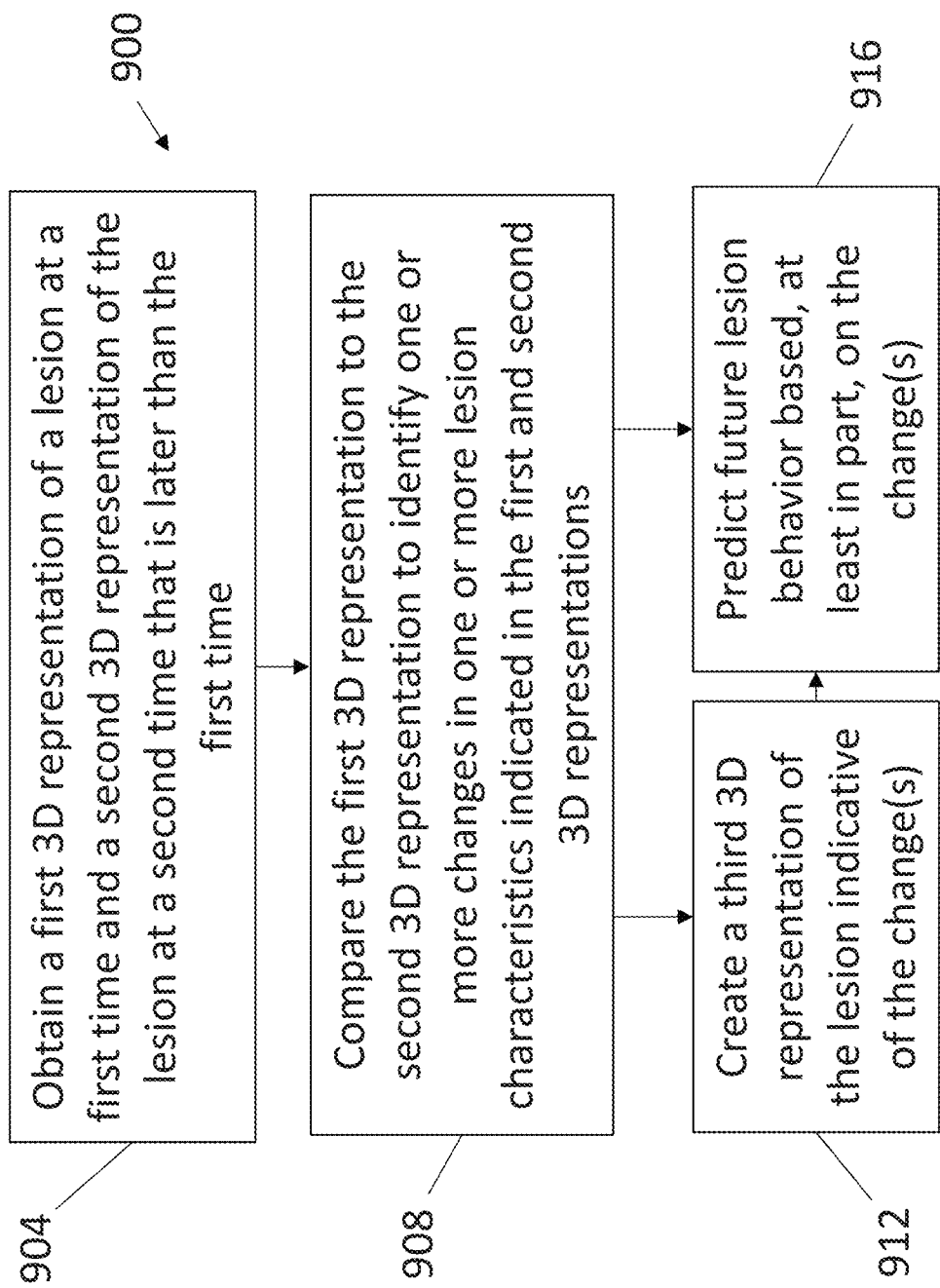
FIG. 9 depicts an exemplary method for using 3D representations of a post-contrast brain lesion to identify one or more changes in one or more of the lesion's characteristics over time.

For example, FIG. 9 depicts a method 900 for using 3D representations of a lesion to identify one or more changes in one or more of the lesion's characteristics over time and, in some instances, predicting future change(s) in those characteristic(s). Method 900 may include a step 904 of obtaining a first 3D representation of a lesion at a first time and a second 3D representation of the lesion at a second time that is later than the first time. The first and second 3D representations may be obtained as described above (e.g., steps 208-220 of method 200) and may—but need not—be images (e.g., method 900 and similar methods require comparison, but not necessarily visualization, of the first and second 3D representations). Time elapsed between the first and second times may be of any suitable duration, such as a matter of days, months, or the like. In some instances, one or more therapies may be administered to the patient during that duration; in this way, the present methods may be used to evaluate the efficacy of those therap(ies).

Figure 10B:
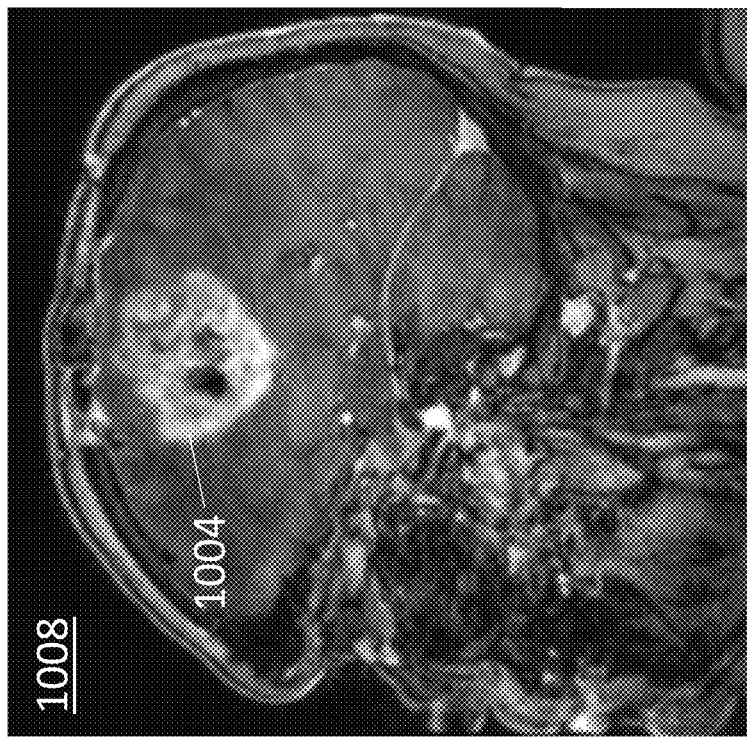
FIGS. 10A-10B are sagittal MRI images of a post-contrast brain lesion taken at a first time and a second, later time, respectively.
Figure 10A:
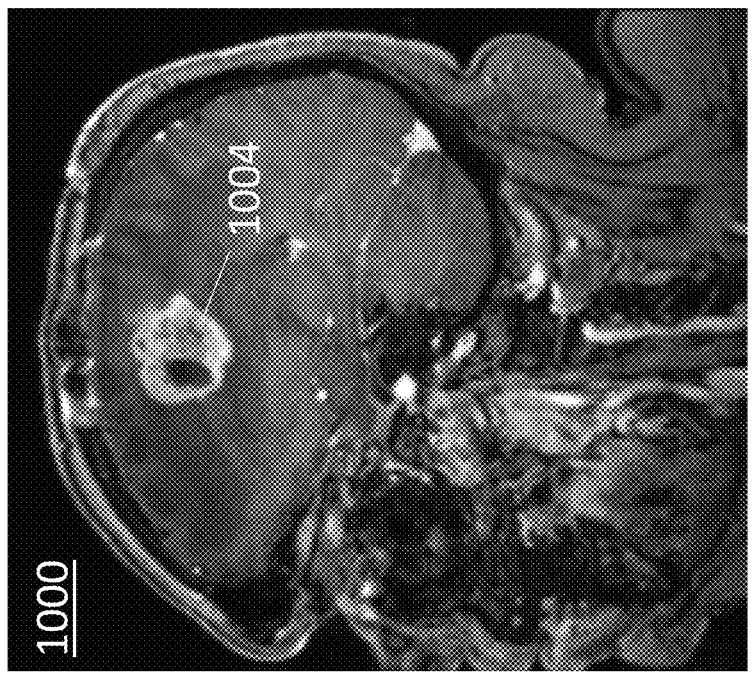

To illustrate, FIGS. 10A and 10B are sagittal MRI images 1000 and 1008 of a lesion 1004, each taken from a respective set of 3D MRI data. The 3D MRI data associated with MRI image 1000 was taken at a first time, and the 3D MRI data associated with MRI image 1008 was taken at a second, later time. From each of the sets of 3D MRI data, a 3D representation of the lesion was created as described above.

At step 908, the first 3D representation may be compared to the second 3D representation to identify one or more changes in one or more of the lesion's characteristics as indicated in the first and second 3D representations. The characteristic(s) may include any of those described above, such as the lesion's shape, geometry, size, topology, volume, surface area, and the like, whether of its outer shell (e.g., 720, FIG. 7B), inner aspect (e.g., 724, FIG. 7B), or both. And such characteristic(s) may each be quantified in any suitable fashion, including in one of the ways described above (e.g., a PCA- or MAT-based quantification, percent coverage, shell thickness, or the like) or another, whether as one value (e.g., a volume or surface area) or an array of values (e.g., representing the characteristic across a surface of or throughout the lesion).

The method of identifying the change(s) may depend on the characteristic being investigated and how it is quantified. As a straightforward example, a surface area, volume, or other characteristic quantified as one value as indicated in the first 3D representation may be directly compared to the same as indicated in the second 3D representation. For further example, in instances where the characteristic is quantified as an array of values, changes in that characteristic between the first and second 3D representations may be identified—in some instances, themselves in an array—by contrasting corresponding values in the array associated with the first 3D representation and the array associated with the second 3D representation.

At step 912, a third 3D representation of the lesion indicative of the change(s) may be created; this step is particularly useful in situations in which the change(s) are identified across a surface of or throughout the lesion. Such indication of the change(s) in the third 3D representation may be via, for example, color or other visually-distinguishable parameter (e.g., if the third 3D representation is an image), an animation, an array of values, or the like. In some methods, the third 3D representation and the second 3D representation may not be consecutively created. To illustrate, the third 3D representation may be prepared simultaneously with the second 3D representation. In some methods, the third 3D representation may comprise the second 3D representation and an indication of the lesion characteristic change(s) between the first and second 3D representations (e.g., the second 3D representation, colored to indicate those change(s)).

Figure 11:
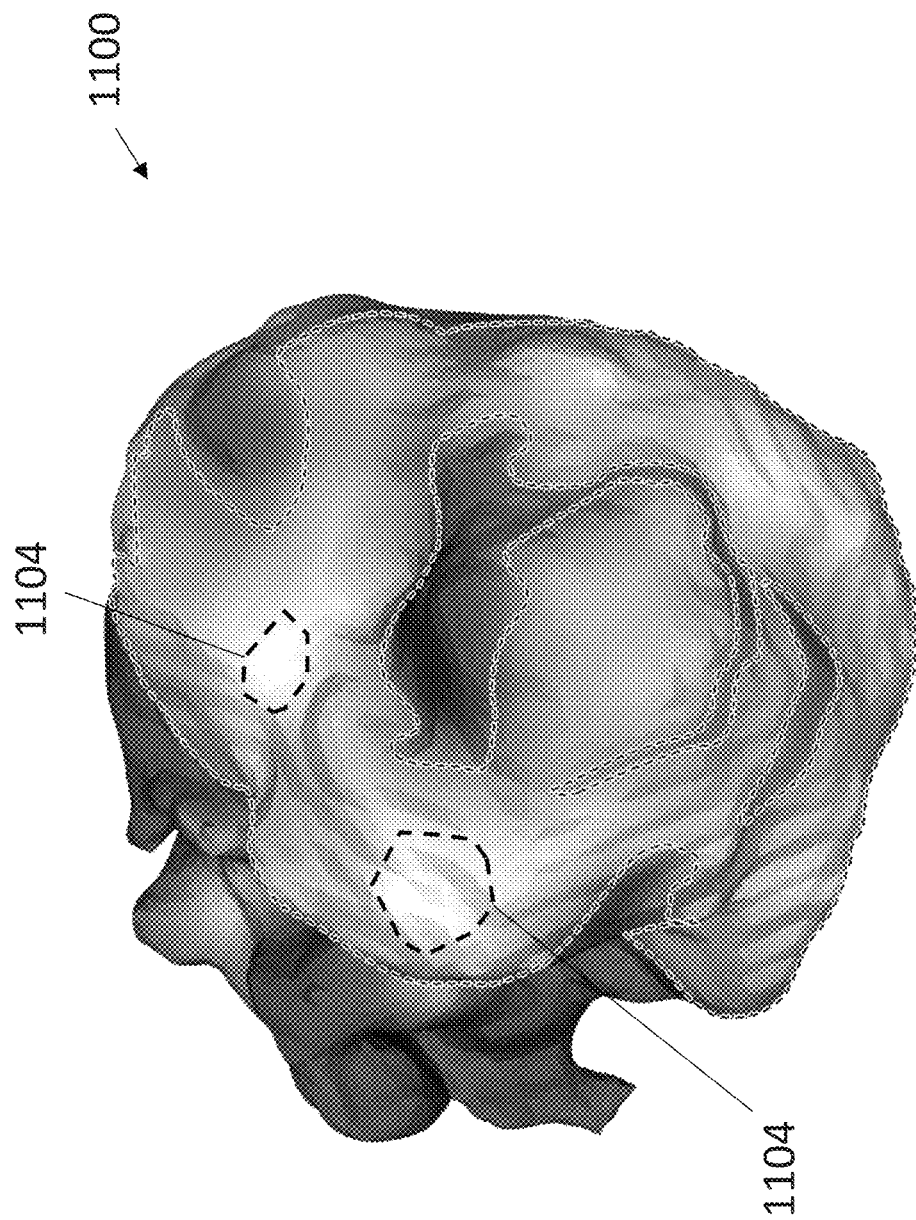
FIG. 11 is a 3D representation of the brain lesion of FIGS. 10A and 10B, indicating changes in its characteristics between the first and second times.

Provided by way of illustration, FIG. 11 depicts a third 3D representation 1100 that is indicative of changes between characteristics of a lesion indicated in a first 3D representation of the lesion associated with a first time (lesion 1004 at the time of FIG. 10A) and a second 3D representation of the lesion associated with a second, later time (lesion 1004 at the time of FIG. 10B). In this example, the characteristics under investigation included the lesion's shape, geometry, size, and topology. Those characteristics were quantified, in each of the first and second 3D representations, as an array of distances, each from a center common to both the first and second 3D representations to a surface of the lesion's outer shell, across that surface. And, to identify the changes in those characteristics, differences between corresponding values in the arrays of distances-displacements-were calculated. In FIG. 11, such displacements are indicated in color, with yellow (in the figures, lighter grey) regions 1104 (e.g., falling within the bold dashed lines) being the largest. As can be seen, this third 3D representation provides more detailed information regarding changes to the lesion's characteristics than would be readily appreciated through conventional study of 2D MRI images.

Figures 12A, 12B:
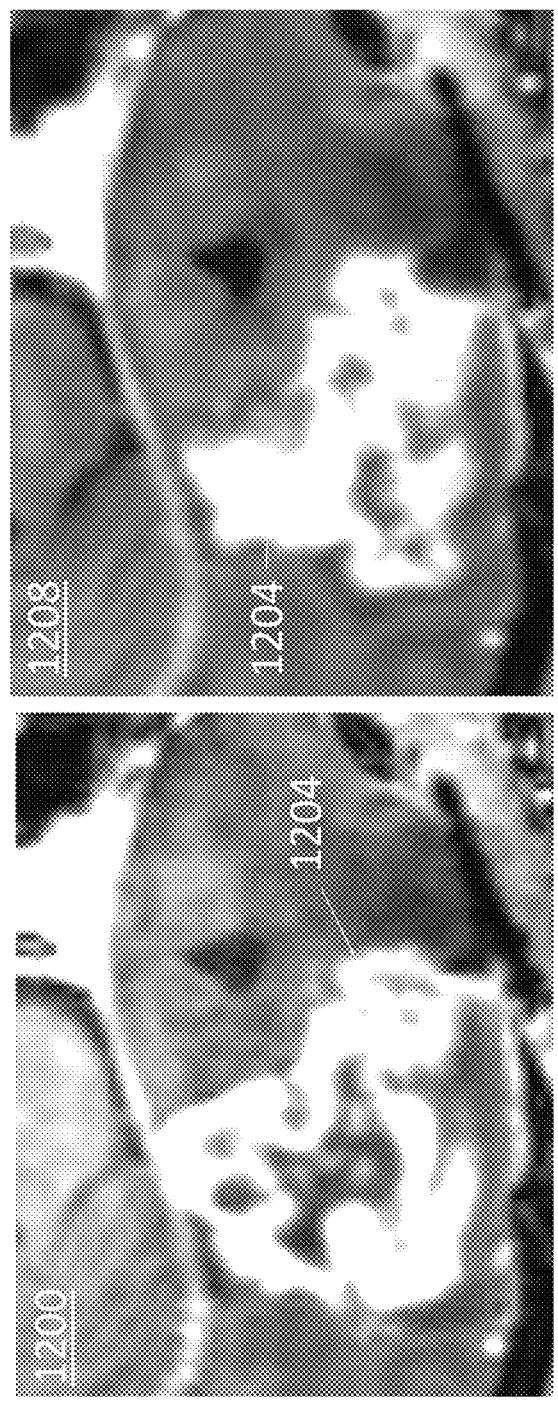
FIGS. 12A-12B are MRI images of a post-contrast brain lesion taken at a first time and a second, later time, respectively.
Figures 12C, 12D:
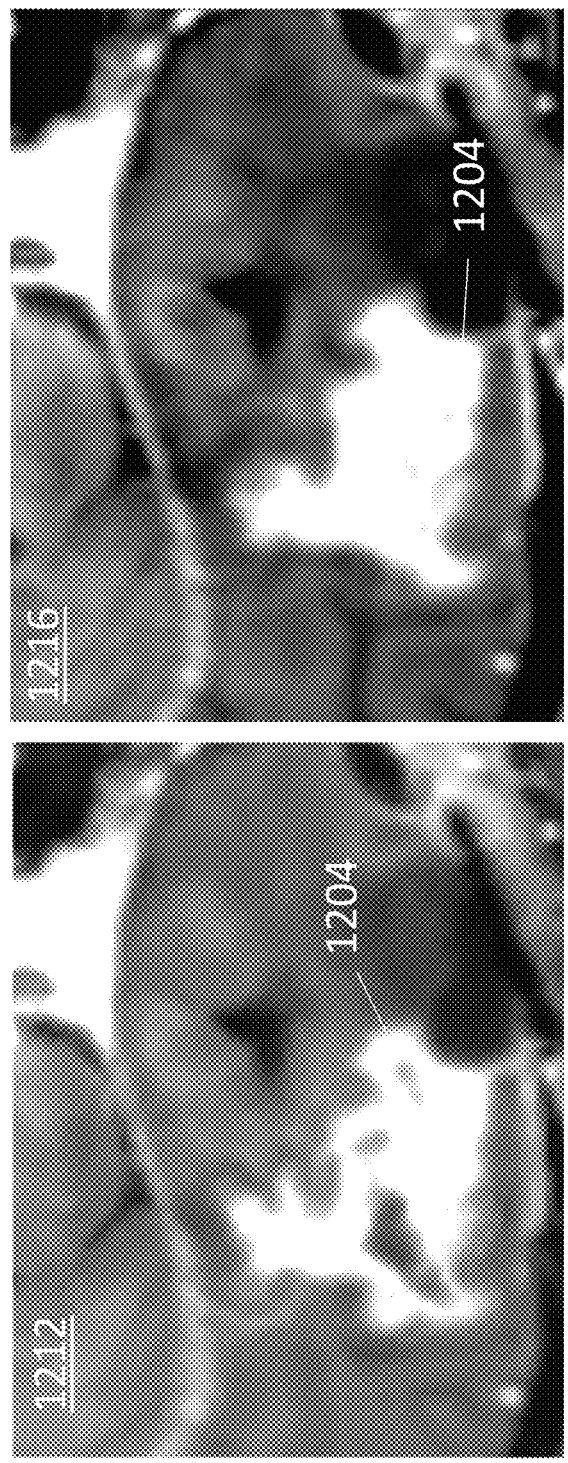
FIG. 12C is a simulated MRI image showing the brain lesion of FIGS. 12A-12B at a third time that is later than the second time, as predicted using an embodiment of the disclosure.
FIG. 12D is an MRI image of the brain lesion of FIGS. 12A-12B at the third time.

In some methods, at step 916, the change(s) can be used to predict future lesion behavior. For example, considering at least the duration between the first and second times, the change(s) can be projected to approximate how the investigated characteristic(s) may change in the future. Provided by way of illustration, FIGS. 12A and 12B are MRI images 1200 and 1208 of a lesion 1204, each taken from a respective set of 3D MRI data. The 3D MRI data associated with MRI image 1200 was taken at a first time, and the 3D MRI data associated with MRI image 1208 was taken at a second, later time. From each of the sets of 3D MRI data, a 3D representation of the lesion was created as described above. By comparing the first and second 3D representations, changes in the lesion's characteristics were identified (e.g., step 908 of method 900). Those changes were then projected to approximate the lesion's characteristics at a third time, later than the second time; that approximation is shown in simulated MRI image 1212 of FIG. 12C. FIG. 12D is an actual MRI image 1216 of lesion 1204 at the third time. By comparing FIGS. 12C and 12D, it can be seen that the simulated and actual lesions have a similar shape and morphology.

It may be appreciated that the functions described above may be performed by multiple types of software applications, such as web applications or mobile device applications. If implemented in firmware and/or software, the functions described above may be stored as one or more instructions or code on a non-transitory computer-readable medium. Examples include non-transitory computer-readable media encoded with a data structure and non-transitory computer-readable media encoded with a computer program. Non-transitory computer-readable media includes physical computer storage media. A physical storage medium may be any available medium that can be accessed by a computer. By way of example, and not limitation, such non-transitory computer-readable media can comprise RAM, ROM, EEPROM, CD-ROM or other optical disk storage, magnetic disk storage or other magnetic storage devices, or any other physical medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above are also included within the scope of non-transitory computer-readable media. Moreover, the functions described above may be achieved through dedicated devices rather than software, such as a hardware circuit comprising custom VLSI circuits or gate arrays, off-the-shelf semiconductors such as logic chips, transistors, or other discrete components, all of which are non-transitory. Additional examples include programmable hardware devices such as field programmable gate arrays, programmable array logic, programmable logic devices or the like, all of which are non-transitory. Still further examples include application specific integrated circuits (ASIC) or very large scale integrated (VLSI) circuits. In fact, persons of ordinary skill in the art may utilize any number of suitable structures capable of executing logical operations according to the described embodiments.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A system for creating a 3-dimensional (3D) representation of a contrast-enhanced brain lesion, the system comprising:
    a computer system comprising a processor and being configured to:
        obtain a first 3D representation of a contrast-enhanced brain lesion generated at a first time;
        obtain a second 3D representation of the contrast-enhanced brain lesion generated at a second time, the second time being later than the first time;
        quantify a change in a characteristic of the contrast-enhanced brain lesion that changed from the first time to the second time, the characteristic comprising the contrast-enhanced brain lesion's shape, geometry, size, topology, volume, or surface area; and
        generate a third 3D representation of the contrast-enhanced brain lesion, the third 3D representation including a visible indication of the change in the characteristic.

2. The system of claim 1, wherein the computer system is configured to:
    quantify a change in each of multiple characteristics of the contrast-enhanced brain lesion that changed from the first time to the second time, the multiple characteristics comprising the contrast-enhanced brain lesion's shape, geometry, size, and topology; and
    generate a third 3D representation of the contrast-enhanced brain lesion that includes a visible indication of each quantified change.

* * * * *